(12) United States Patent
Ghosh

(10) Patent No.: US 11,633,607 B2
(45) Date of Patent: Apr. 25, 2023

(54) AV SYNCHRONOUS SEPTAL PACING

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 414 days.

(21) Appl. No.: 16/521,000

(22) Filed: Jul. 24, 2019

(65) Prior Publication Data
US 2021/0023367 A1    Jan. 28, 2021

(51) Int. Cl.
*A61N 1/368* (2006.01)
*A61N 1/375* (2006.01)
*A61N 1/05* (2006.01)

(52) U.S. Cl.
CPC .......... *A61N 1/368* (2013.01); *A61N 1/0573* (2013.01); *A61N 1/3756* (2013.01); *A61N 1/37512* (2017.08); *A61N 1/37518* (2017.08)

(58) Field of Classification Search
CPC .. A61N 1/368; A61N 1/0573; A61N 1/37512; A61N 1/37518; A61N 1/3756; A61N 1/0563; A61N 1/37241; A61N 1/3622; A61B 5/318
See application file for complete search history.

(56) References Cited

U.S. PATENT DOCUMENTS

| | | | |
|---|---|---|---|
| 6,980,675 | B2 | 12/2005 | Evron et al. |
| 7,164,948 | B2 | 1/2007 | Struble et al. |
| 7,286,866 | B2 | 10/2007 | Okerlund et al. |
| 7,308,297 | B2 | 12/2007 | Reddy et al. |
| 7,308,299 | B2 | 12/2007 | Burrell et al. |
| 7,321,677 | B2 | 1/2008 | Evron et al. |
| 7,321,798 | B2 | 1/2008 | Muhlenberg et al. |
| 7,340,288 | B1 | 3/2008 | Karicherla et al. |
| 7,346,381 | B2 | 3/2008 | Okerlund et al. |
| 7,454,248 | B2 | 11/2008 | Burrell et al. |
| 7,499,743 | B2 | 3/2009 | Vass et al. |
| 7,565,190 | B2 | 7/2009 | Okerlund et al. |
| 7,587,074 | B2 | 9/2009 | Zarkh et al. |
| 7,599,730 | B2 | 10/2009 | Hunter et al. |
| 7,613,500 | B2 | 11/2009 | Vass et al. |
| 7,742,629 | B2 | 6/2010 | Zarkh et al. |
| 7,747,047 | B2 | 6/2010 | Okerlund et al. |

(Continued)

OTHER PUBLICATIONS

International Search Report and Written Opinion from PCT Application No. PCT/US2020/041882, dated Nov. 2, 2020, 10 pages.

*Primary Examiner* — Mark W. Bockelman
(74) *Attorney, Agent, or Firm* — Mueting Raasch Group

(57) ABSTRACT

An implantable medical system may provide atrioventricular synchronous pacing using the ventricular septal wall. The system may include a ventricular electrode coupled to an intracardiac housing or a first medical lead implantable in the ventricular septal wall of the patient's heart to deliver cardiac therapy to or sense electrical activity of the left ventricle of the patient's heart and a right atrial electrode coupled to a leadlet or second medical lead to deliver cardiac therapy to or sense electrical activity of the right atrium of the patient's heart. A right ventricular electrode may be coupled to the intracardiac housing or the first medical lead and implantable in the ventricular septal wall of the patient's heart to deliver cardiac therapy to or sense electrical activity of the right ventricle of the patient's heart.

16 Claims, 13 Drawing Sheets

(56) References Cited

U.S. PATENT DOCUMENTS

| | | |
|---|---|---|
| 7,778,685 B2 | 8/2010 | Evron et al. |
| 7,778,686 B2 | 8/2010 | Vass et al. |
| 7,813,785 B2 | 10/2010 | Okerlund et al. |
| 7,996,063 B2 | 8/2011 | Vass et al. |
| 8,060,185 B2 | 11/2011 | Hunter et al. |
| 8,401,616 B2 | 3/2013 | Verard et al. |
| 8,634,912 B2 | 1/2014 | Bornzin et al. |
| 8,700,181 B2 | 4/2014 | Bornzin et al. |
| 8,731,642 B2 | 5/2014 | Zarkh et al. |
| 8,861,830 B2 | 10/2014 | Brada et al. |
| 8,914,131 B2 | 12/2014 | Bornzin et al. |
| 8,996,109 B2 | 3/2015 | Karst et al. |
| 9,119,959 B2 | 9/2015 | Rys et al. |
| 9,320,446 B2 | 4/2016 | Gillberg et al. |
| 9,675,579 B2 | 6/2017 | Rock et al. |
| 9,877,789 B2 | 1/2018 | Ghosh |
| 9,924,884 B2 | 3/2018 | Ghosh et al. |
| 10,064,567 B2 | 9/2018 | Ghosh et al. |
| 10,251,555 B2 | 4/2019 | Ghosh et al. |
| 10,335,589 B2 | 7/2019 | Kim |
| 2005/0008210 A1 | 1/2005 | Evron et al. |
| 2006/0074285 A1 | 4/2006 | Zarkh et al. |
| 2008/0294229 A1 | 11/2008 | Friedman et al. |
| 2010/0298841 A1 | 11/2010 | Prinzen et al. |
| 2013/0116741 A1 | 5/2013 | Bornzin et al. |
| 2013/0123872 A1 | 5/2013 | Bornzin et al. |
| 2014/0107723 A1 | 4/2014 | Hou et al. |
| 2014/0371833 A1 | 12/2014 | Ghosh et al. |
| 2016/0310726 A1 | 10/2016 | Demmer et al. |
| 2018/0050208 A1 | 2/2018 | Shuros et al. |
| 2019/0083779 A1 | 3/2019 | Yang et al. |

AV SYNCHRONOUS SEPTAL PACING

The present technology is related generally to implantable medical systems and methods and, in particular, to synchronous pacing of a patient's heart.

The cardiac conduction system includes the sinus atrial (SA) node, the atrioventricular (AV) node, the bundle of His, bundle branches, and Purkinje fibers. A heartbeat is initiated in the SA node, which may be described as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Patients with a conduction system abnormality, such as poor AV node conduction or poor SA node function, may receive an implantable medical device (IMD), such as a pacemaker, to restore a more normal heart rhythm and AV synchrony. Some types of IMDs, such as cardiac pacemakers, implantable cardioverter defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart, and control the delivery of therapeutic stimulation to the heart based on the sensing.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in different ventricles of the heart. Significant differences in timing of contractions can reduce cardiac efficiency. CRT, delivered by an IMD to the heart, may enhance cardiac output by resynchronizing the electromechanical activity of the ventricles of the heart. CRT is sometimes referred to as "triple chamber pacing" because CRT delivers pacing to three chambers, namely, the right atrium, right ventricle, and left ventricle.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP), a painless therapy, can be used to treat ventricular tachycardia (VT) to substantially terminate many monomorphic fast rhythms. While ATP is painless, ATP may not deliver effective therapy for all types of VTs. For example, ATP may not be as effective for polymorphic VTs, which has variable morphologies. Polymorphic VTs and ventricular fibrillation (VFs) can be more lethal and may require expeditious treatment by shock.

Dual chamber medical devices are available that include a transvenous atrial lead carrying electrodes that may be placed in the right atrium and a transvenous ventricular lead carrying electrodes that may be placed in the right ventricle via the right atrium. The dual chamber medical device itself is generally implanted in a subcutaneous pocket and the transvenous leads are tunneled to the subcutaneous pocket. A dual chamber medical device may sense atrial electrical signals and ventricular electrical signals and can provide both atrial pacing and ventricular pacing as needed to promote a normal heart rhythm and AV synchrony. Some dual chamber medical devices can treat both atrial and ventricular arrhythmias.

Intracardiac medical devices, such as a leadless pacemaker, have been introduced or proposed for implantation entirely within a patient's heart, eliminating the need for transvenous leads. A leadless pacemaker may include one or more electrodes on its outer housing to deliver therapeutic electrical signals and/or sense intrinsic depolarizations of the heart. Intracardiac medical devices may provide cardiac therapy functionality, such as sensing and pacing, within a single chamber of the patient's heart. Single chamber intracardiac devices may also treat either atrial or ventricular arrhythmias or fibrillation. Some leadless pacemakers are not intracardiac and may be positioned outside of the heart and, in some examples, may be anchored to a wall of the heart via a fixation mechanism.

In some patients, single chamber devices may adequately address the patient's needs. However, single chamber devices capable of only single chamber sensing and therapy may not fully address cardiac conduction disease or abnormalities in all patients, for example, those with some forms of AV dyssynchrony.

SUMMARY

The techniques of this disclosure generally relate to implantable medical systems and methods for synchronous pacing of a patient's heart using the ventricular septal wall. These techniques may facilitate a reduction in possible infections and facilitate ease of implantation for cardiac therapy, especially cardiac resynchronization therapy, by using fewer leads than existing leaded systems. Implantable medical systems may include a right-atrial electrode and a ventricular electrode and provide dual- or triple-chamber pacing of the patient's heart. At least one of the electrodes may be coupled to a leadlet, e.g., extending across or through the tricuspid valve. The ventricular electrode may pace the left-ventricular septal wall. A right ventricular electrode may also be included on the same device as the ventricular electrode. Some systems may provide dual- or triple-chamber pacing using an intracardiac device and, in some cases, only one intracardiac device. Some of the illustrative implantable medical systems may provide such pacing without needing to create a subcutaneous pocket or without using a separate device having leads.

In one aspect, the present disclosure provides a leadless implantable medical device for a patient's heart includes an intracardiac housing implantable in the right ventricle of the patient's heart, a leadlet coupled to the intracardiac housing extendable through the tricuspid valve of the patient's heart into the right atrium of the patient's heart, and a plurality of electrodes coupled to one or both of the intracardiac housing and the leadlet. The plurality of electrodes includes a ventricular electrode implantable in the ventricular septal wall of the patient's heart to deliver cardiac therapy to or sense electrical activity of the left ventricle of the patient's heart. The plurality of electrodes also includes a right atrial electrode coupled to the leadlet and implantable to deliver cardiac therapy to or sense electrical activity of the right atrium of the patient's heart. The device further includes a therapy delivery circuit operably coupled to the plurality of electrodes to deliver cardiac therapy to the patient's heart, a sensing circuit operably coupled to the plurality of electrodes to sense electrical activity of the patient's heart, and a controller having processing circuitry operably coupled to the therapy delivery circuit and the sensing circuit. The controller is configured to monitor electrical activity using one or both of the right atrial electrode and the ventricular electrode and deliver cardiac therapy based on the monitored electrical activity.

In another aspect, the present disclosure provides an implantable medical system including an intracardiac housing implantable in a right ventricle of a patient's heart, an implantable medical lead implantable into the right atrium of a patient's heart, and a plurality of electrodes. The plurality of electrodes includes a ventricular electrode coupled to the intracardiac housing and implantable in the ventricular septal wall of the patient's heart to deliver cardiac therapy to or sense electrical activity of the left ventricle of the patient's heart. The plurality of electrodes includes a right atrial electrode coupled to the lead and implantable to deliver cardiac therapy to or sense electrical activity of the right atrium of the patient's heart. The system further includes a first controller contained in the intracardiac housing and having processing circuitry operably coupled to the ventricular electrode. The system further includes a second controller coupled to the implantable medical lead and having processing circuitry operably coupled to the right atrial electrode. The first controller is configured to wirelessly communicate with the second controller to monitor electrical activity using one or both of the right atrial electrode and the ventricular electrode and deliver cardiac therapy based on the monitored electrical activity.

In another aspect, the present disclosure provides an implantable medical device including an implantable medical housing for a patient's heart, a first medical lead coupled to the implantable medical housing and implantable in the ventricular septal wall through the right ventricle of the patient's heart, a second medical lead coupled to the implantable medical housing and implantable in the right atrium of the patient's heart, and a plurality of electrodes. The plurality of electrodes includes a left ventricular electrode coupled to the first medical lead and implantable in the ventricular septal wall of the patient's heart to deliver cardiac therapy to or sense electrical activity of the left ventricle of the patient's heart, a right ventricular electrode coupled to the first medical lead and implantable in the ventricular septal wall of the patient's heart to deliver cardiac therapy to or sense electrical activity of the right ventricle of the patient's heart, and a right atrial electrode coupled to the second medical lead and implantable to deliver cardiac therapy to or sense electrical activity of the right atrium of the patient's heart. The device includes a controller having processing circuitry operably coupled to the ventricular electrode and to the right atrial electrode. The controller is configured to monitor electrical activity using one or more of the left ventricular electrode, the right ventricular electrode, and the right atrial electrode. The controller is also configured to deliver cardiac therapy based on the monitored electrical activity.

In another aspect, the present disclosure provides a method that includes implanting a ventricular electrode coupled to an intracardiac housing or a first medical lead to the ventricular septal wall of a patient's heart to deliver cardiac therapy to or sense electrical activity of the ventricle of the patient's heart, implanting a right atrial electrode coupled to a leadlet or a second medical lead in the right atrium of the patient's heart to deliver cardiac therapy to or sense electrical activity of the right atrium of the patient's heart, monitoring electrical activity using the ventricular electrode, the right atrial electrode, or both, and delivering cardiac therapy based on the monitored electrical activities using at least one of the ventricular electrode or the right atrial electrode.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
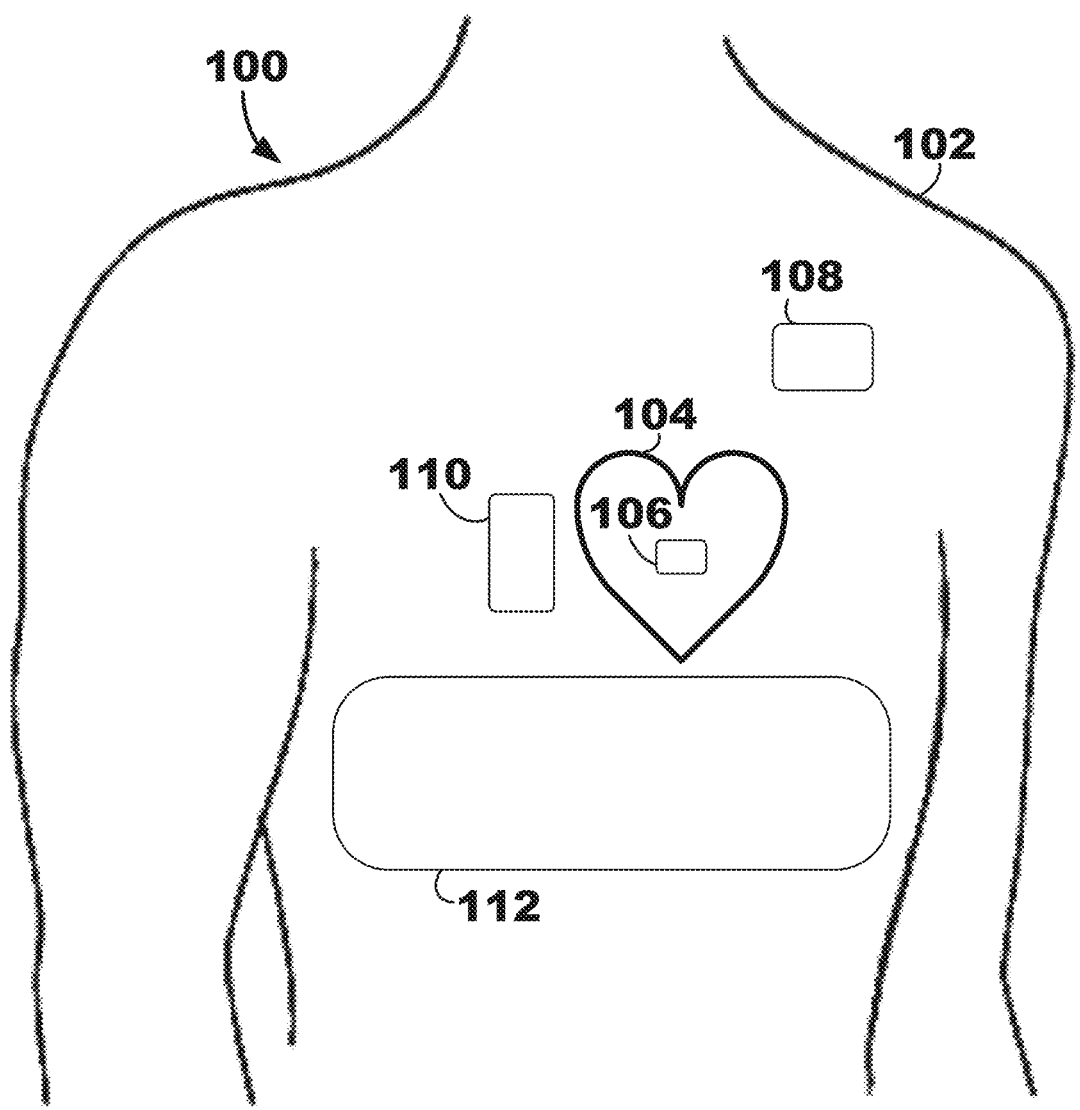
FIG. 1 is a diagram that illustrates an implantable medical system that may be used to provide cardiac therapy to a patient.

The present disclosure provides implantable medical systems and methods for synchronous pacing of a patient's heart using the ventricular septal wall, or ventricular septum. Techniques of this disclosure may facilitate a reduction in possible infections and facilitate ease of implantation for cardiac therapy, especially cardiac resynchronization therapy (CRT), by using fewer leads than existing leaded systems. Implantable medical systems may include a right-atrial electrode and a ventricular electrode and provide dual- or triple-chamber pacing of the patient's heart. At least one of the electrodes may be coupled to a leadlet. The ventricular electrode may pace the left-ventricular septal wall. A right ventricular electrode may also be included on the same device as the ventricular electrode. Some systems may provide dual- or triple-chamber pacing using an intracardiac device and, in some cases, only one intracardiac device. Some of the illustrative implantable medical systems may provide such pacing without needing to create a subcutaneous pocket or without using a separate device having leads.

As used herein, the term "or" is generally employed in its inclusive sense, for example, to mean "and/or" unless the context clearly dictates otherwise. The term "and/or" means one or all the listed elements or a combination of at least two of the listed elements.

The terms "coupled" or "connected" refer to elements being attached to each other either directly (i.e., in direct contact with each other) or indirectly (i.e., having one or more elements between and attaching the two elements). Either term may be modified by "operatively" and "operably," which may be used interchangeably, to describe that the coupling or connection is configured to allow the components to interact to carry out functionality described in this disclosure or known to one skilled in the art having the benefit of this disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

Figure 2:
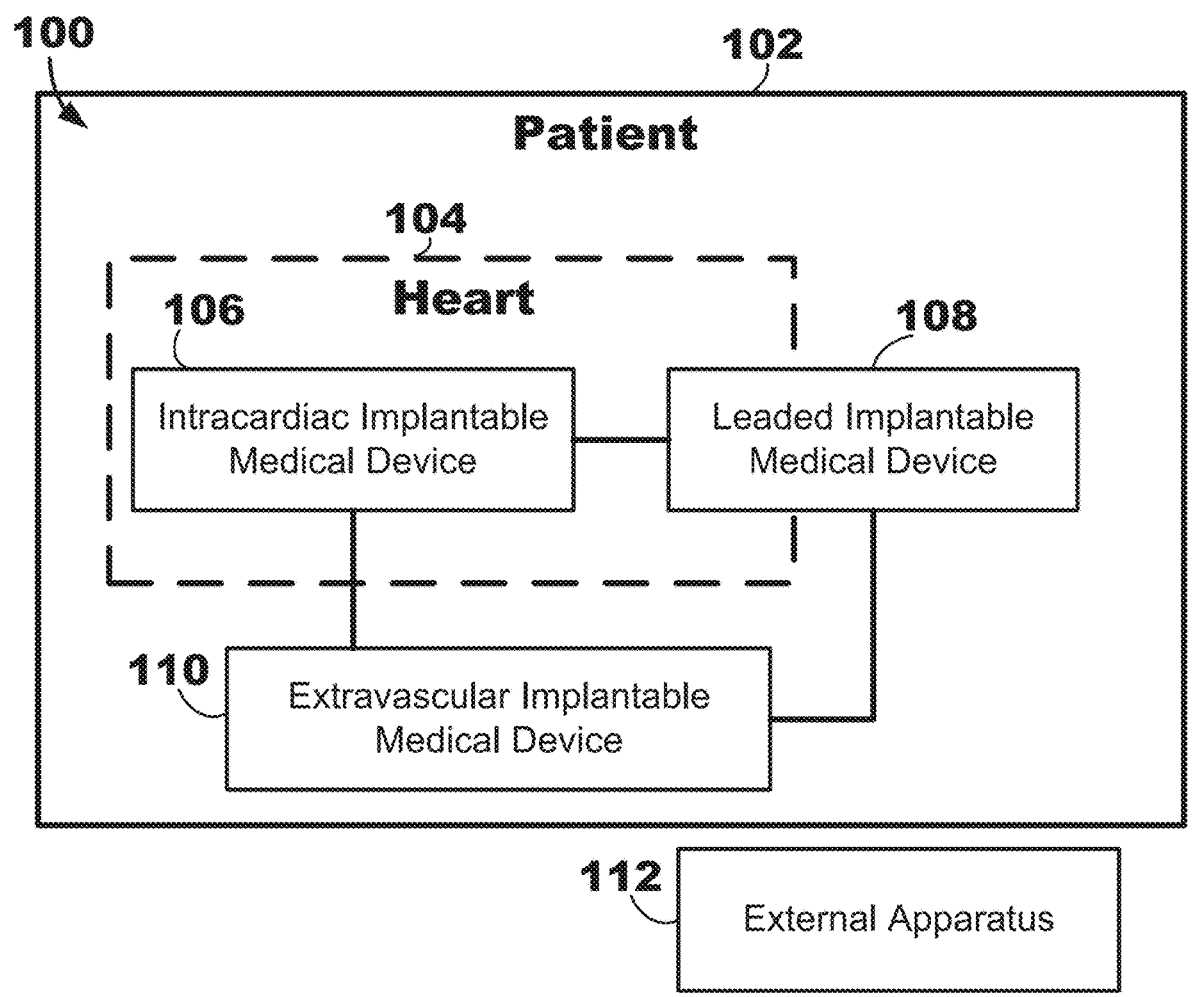
FIG. 2 is a schematic diagram that illustrates the implantable medical system of FIG. 1.

FIGS. 1-2 show one example of an implantable medical system that may be used to provide single- or multiple-chamber pacing to deliver cardiac therapy to a patient. FIG. 1 illustrates some examples of various locations for devices or components of the system relative to the patient, and FIG. 2 illustrates a schematic depiction of the system and the patient.

As illustrated, an implantable medical system 100 may be coupled to the body of a patient 102. In general, the system 100 may monitor electrical activity, or other activity, of the heart 104 of the patient 102 (or the patient's heart) and may deliver cardiac therapy based on the monitored electrical activity. The system 100 may provide various types of cardiac therapy, such as CRT using multiple-chamber pacing, for example, dual- or triple-chamber synchronous pacing, using one or more of the devices or components in the system 100. In particular, the system 100 may deliver atrioventricular (AV) synchronous pacing to two or more chambers of the heart 104. In one example, the system 100 may deliver pacing to each of the left ventricle (LV), the right ventricle (RV), and the right atrium (RA) to facilitate, e.g., three-chamber synchronous pacing.

The system 100 may include any number of components to deliver AV synchronous pacing such as one or more of an intracardiac implantable medical device 106 (or intracardiac IMD), a leaded implantable medical device 108 (or leaded IMD), an extravascular implantable medical device 110 (or extravascular IMD), and an external apparatus 112. In general, one or more of these devices include one or more electrodes. One or more of these devices of the system 100 may be capable of, individually or cooperatively, monitoring electrical activity of the heart 104 and delivering cardiac therapy based on the monitored electrical activity.

The intracardiac IMD 106 may be implanted in one or more chambers of the heart 104. As used herein, an "intracardiac" device refers to a device configured to be implanted entirely within the heart 104. In one example, the intracardiac IMD 106 is implanted in the RV of the heart 104.

The intracardiac IMD 106 may be described as a leadless IMD. As used herein, a "leadless" device refers to a device being free of a lead extending out of the heart 104. In other words, a leadless device may have a lead that does not extend from outside of the patient's heart to inside of the patient's heart. Some leadless devices may be introduced through a vein, but once implanted, the device is free of, or may not include, any transvenous lead and may be configured to provide cardiac therapy without using any transvenous lead. In one example, a leadless device implanted in the RV, in particular, does not use a lead to operably connect to an electrode in the ventricle when a housing of the device is positioned in the RV.

One or more electrodes may be directly or indirectly coupled to an intracardiac housing of the intracardiac IMD 106. One or more of the electrodes may be leadless. As used herein, a "leadless" electrode refers to an electrode operably coupled to a device being free of a lead, or without using a lead, extending between the electrode and the housing of the device.

The intracardiac IMD 106 may include one or more leadlets. As used herein, the term "leadlet" refers to an elongate structure that extends from a housing of a device implanted in the patient's heart 104 and remains within the patient's heart. In other words, a leadlet does not extend outside of the patient's heart 104. In some cases, a leadlet may extend from one chamber of the heart 104 to another chamber of the heart. For example, a proximal end of a leadlet may be coupled to the housing of an intracardiac device implanted in the RV and a body of the leadlet may extend through the tricuspid valve such that a distal end of the leadlet is positioned or implanted in the RA.

The leaded IMD 108 includes one or more implantable medical leads coupled to an implantable medical housing of the leaded IMD and may include one or more electrodes implantable in the heart 104. The one or more electrodes may be directly or indirectly coupled to the housing of the leaded IMD 108. For example, one or more of the electrodes may be leaded, or indirectly coupled to the housing by a lead, to the housing of the leaded IMD 108. Any suitable type of leaded IMD 108 may be used, such as a leaded pacemaker.

The one or more electrodes may be implanted in one or more chambers of the heart 104. In one example, the leaded IMD 108 may include, or have, an RA electrode implanted in the RA of the heart 104 via an RA lead. In another example, the leaded IMD 108 may include, or have, an RA lead coupled to an RA electrode implantable in the RA. Further, the leaded IMD 108 may include, or have, a RV lead coupled to an RV electrode implanted in the RV and an LV electrode implanted in the LV.

The housing, or can, of the leaded IMD 108 may be implanted in an extravascular location outside of the heart 104. For example, the housing of the leaded IMD 108 may be implanted in a subcutaneous pocket of the patient 102. In this manner, when implanted, portions of the leaded IMD 108 may be positioned in the heart 104 and other portions of the leaded IMD may be positioned outside the heart.

The extravascular IMD 110 is implanted in an extravascular location outside of the heart 104. For example, the extravascular IMD 110 may be implanted in a subcutaneous pocket of the patient 102. The extravascular IMD 110 may include a housing, or can, and may include one or more leads. Typically, the extravascular IMD 110 does not include a portion that extends into the heart 104. Any suitable type of extravascular IMD 110 may be used, which may include or be described as an extravascular implantable cardioverter defibrillator (EVICD) or a subcutaneous device (SD).

The extravascular IMD 110 may provide particular types of cardiac therapy to the heart 104. For example, the intracardiac IMD 106 or leaded IMD 108 may wirelessly communicate with the extravascular IMD 110 to trigger shock therapy (e.g., defibrillation) performed using the extravascular IMD. Wireless communication between the IMDs 106, 108 and the IMD 110 may use a distinctive, signaling, or triggering electrical pulse provided by an RA electrode of the intracardiac IMD 106 or leaded IMD 108 that conducts through the patient's tissue and is detectable by the extravascular IMD 110. Further, such wireless communication may use a communication interface, which may include an antenna, of the intracardiac IMD 106 or the leaded IMD 108 to provide electromagnetic radiation that propagates through patient's tissue and is detectable, for example, using a communication interface, which may also include an antenna, of the extravascular IMD 110.

The external apparatus 112 may include one or more components to facilitate evaluation of various implantation locations (e.g., spatial location, implant depth, etc.) and/or pacing settings (e.g., pulse width, pulse timing, pulse amplitude, etc.). For example, implantation location of and/or pacing delivered by one or more electrodes of the intracardiac IMD 106, leaded IMD 108, or extravascular IMD 110 may be evaluated using the external apparatus 112. The external apparatus 112 may include one or more of an electrode apparatus, a display apparatus, and a computing apparatus as will be described further herein with respect to FIGS. 9-11. In one example, the electrode apparatus of the external apparatus 112 may include a plurality of electrodes configured to provide electrical heterogeneity information (EHI) that may be used to evaluate the various implantation locations and/or paced settings.

In general, any one or more of the components of the system 100 may communicate with one another, e.g., wired or wirelessly. One or more of the devices 106, 108, 110 may include a controller having a communication interface and processing circuitry. For example, the intracardiac IMD 106 may be operably coupled to the leaded IMD 108 or the extravascular IMD 110 to communicate wirelessly. The leaded IMD 108 may be operably coupled to the extravascular IMD 110 to communicate wirelessly. The controller of each device may be operably coupled to various other devices and/or components, such as the electrodes of the respective device or apparatus.

In some embodiments, to provide synchronous AV septal pacing, the RA electrode senses the intrinsic atrial electrical activity or paces the atrium, and the RV and LV electrodes pace the RV and LV respectively at a programmed interval (AV interval) after the atrial sensing or pacing event for each cardiac cycle. There may be also a programmed electrical delay between the RV and LV electrodes (VV delay), so that pacing of the two ventricles is sequential instead of simultaneous. The extravascular IMD may have additional sensing capabilities for intrinsic atrial electrical activation and may send an intrabody signal (such as a signaling pulse) to trigger pacing in the ventricle at a programmed time-interval following the atrial event. The extravascular IMD may also have sensing capabilities for ventricular electrical events and coupled with an extravascular defibrillation lead that can defibrillate on detection of ventricular tachycardia.

One or more of the components of the system 100 or devices of the system 100, such as intracardiac IMD 106, leaded IMD 108, extravascular IMD 110, or external apparatus 112, described herein may include a controller having processing circuitry or processor, such as a central processing unit (CPU), computer, logic array, or other device capable of directing data coming into or out of the system, device, or apparatus. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

Processing circuitry of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components, such as relays and timers to achieve the desired results, either alone or in combination with a microprocessor-based system.

The exemplary systems, devices, apparatus, methods, and other functionality may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other systems, devices, apparatus, and/or methods. In view of the above, it will be readily apparent that the controller functionality as described herein may be implemented in any manner known to one skilled in the art having the benefit of the present disclosure.

The system 100 may be employed in various configurations to provide cardiac therapy. For example, the system 100 may utilize the LV side of the ventricular septal wall, or ventricular septum, to provide CRT. In one example, the system 100 may include the intracardiac IMD 106 configured to pace both the RV and LV sides of the ventricular septal wall, or RV septum and LV septum, respectively, without using transvenous leads or without creating a subcutaneous pocket.

Further, for example, the system 100 including intracardiac IMD 106 may be configured as a completely intracardiac implantable medical system. In one example, the system 100 may be configured to pace the LV septum with or without pacing the RV septum. In another example, the housing of the intracardiac IMD 106 may be implanted in the RV endocardium with a screw-in helix to penetrate the RV septum to pace the LV septum or both the RV and LV septa, which may allow for LV endocardial septal pacing with an intracardiac pacemaker without exposing the device to the LV blood volume, or LV endocardial blood pool. The intracardiac IMD 106 may further include a leadlet that can be fixated in the right atrium for right atrial sensing/pacing.

In one particular example, the intracardiac IMD 106 of the system 100 that is configured to pace the LV septum for CRT may include an intracardiac housing implanted in the endocardial RV septum and a helix or screw-in mechanism for penetrating the ventricular septum with a pacing electrode to pace the LV septum. The intracardiac IMD 106 may be configured to pace both the RV septum and the LV septum or apex, or just the LV septum or apex, without exposing an electrode or other component directly to the LV blood volume. The intracardiac IMD 106 may be triggered by another device, such as the leaded IMD 108 or the extravascular IMD 110, that senses electrical activity of the patient's heart (e.g., P-waves, etc.). The intracardiac IMD 106 may include a leadlet extending through the tricuspid valve from the RV into the RA that may be fixated to the RA for sensing or pacing of the RA, which may be described as providing a complete intracardiac DDD-biventricular pacemaker.

In another example, the system 100 may include only the leaded IMD 108. In yet another example, the system 100 may include both the intracardiac IMD 106 and the leaded IMD 108.

Figure 3:
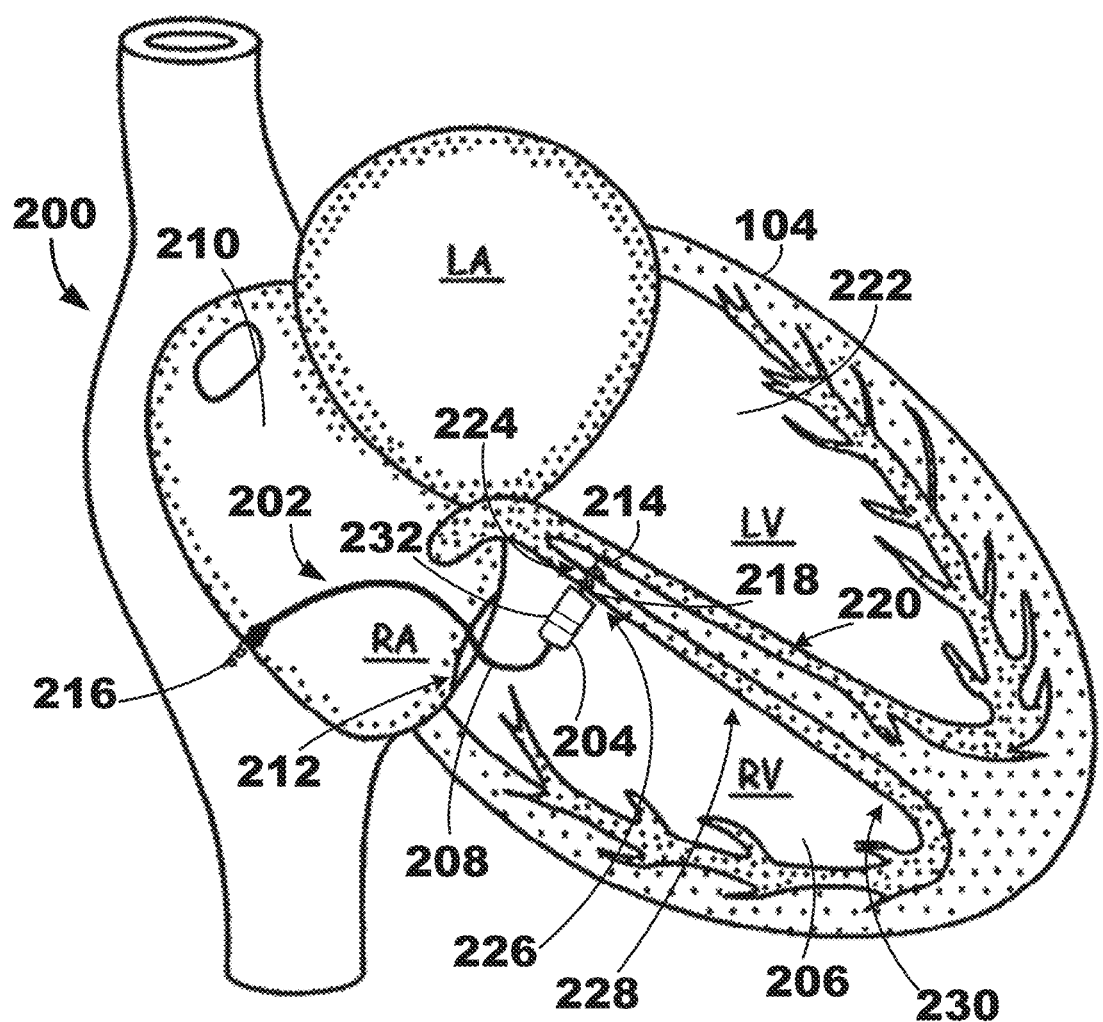
FIG. 3 is a cross-sectional diagram that illustrates a first example of the implantable medical system of FIG. 1 including an intracardiac medical device with a leadlet.
Figure 4:
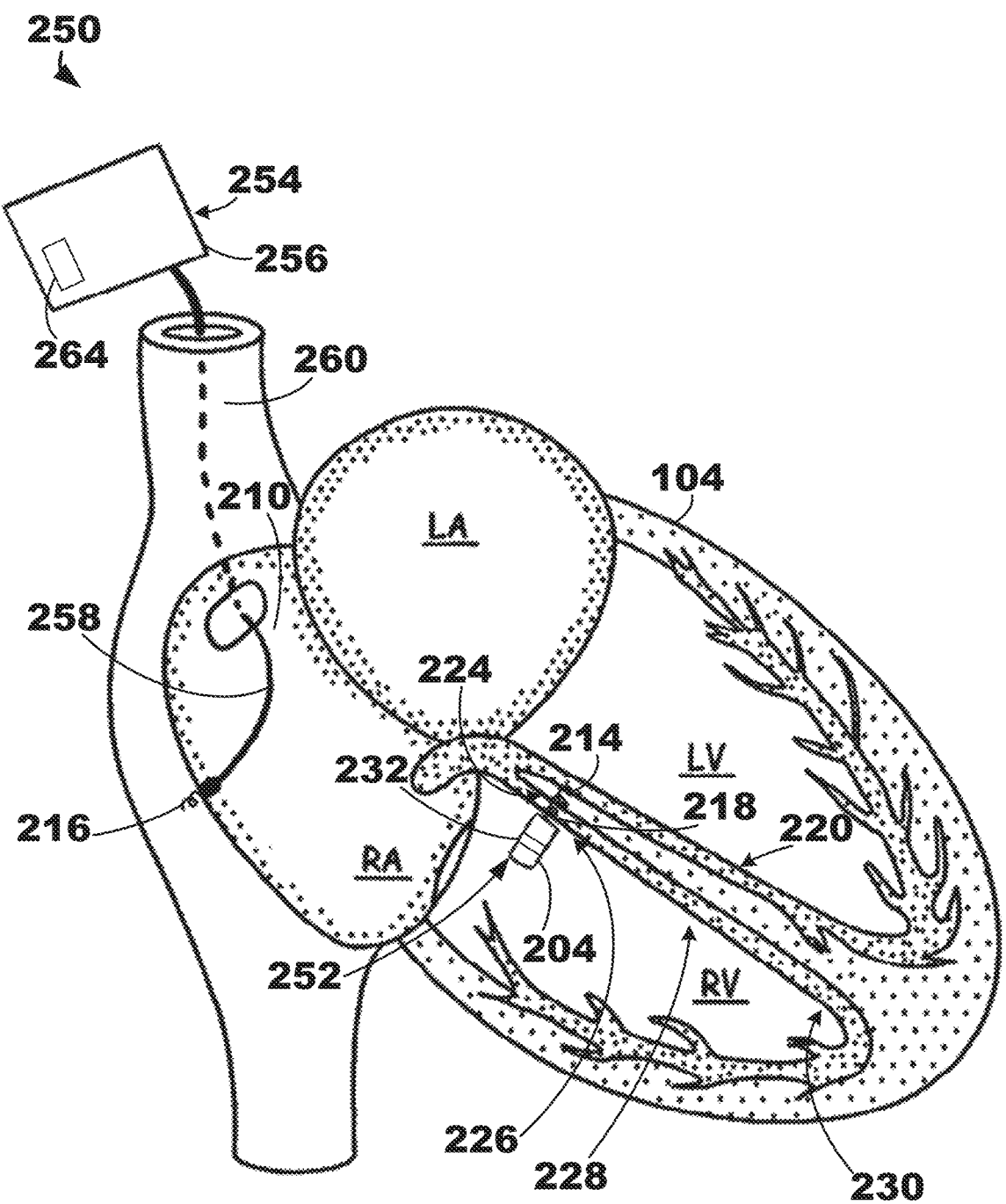
FIG. 4 is a cross-sectional diagram that illustrates a second example of the implantable medical system of FIG. 1 including an intracardiac medical device and a leaded medical device.
Figure 5:
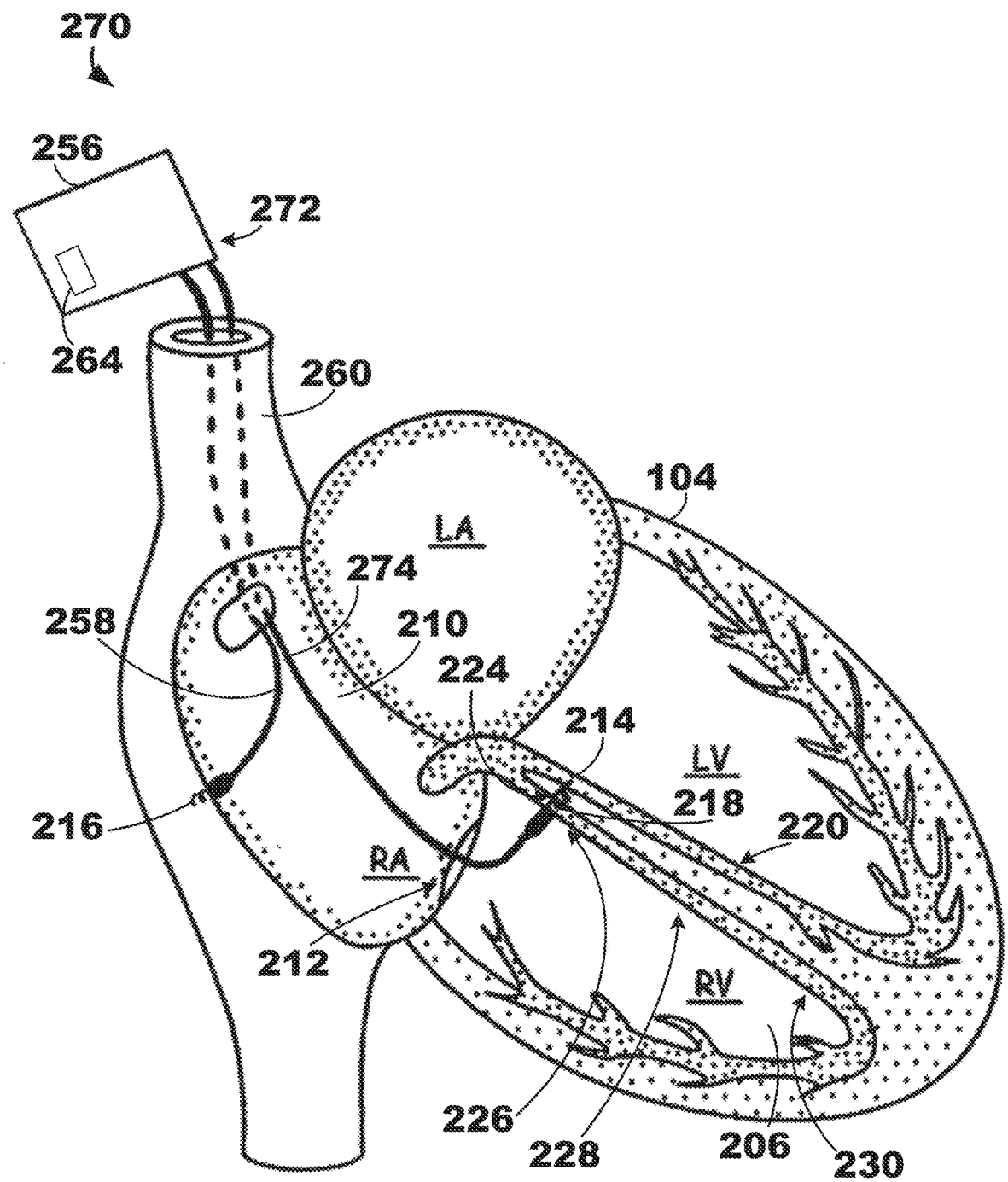
FIG. 5 is a cross-sectional diagram that illustrates a third example of the implantable medical system of FIG. 1 including a leaded medical device.

FIGS. 3-5 show various examples of configurations of the implantable medical system 100 including particular examples of one or both of the intracardiac IMD 106 and the leaded IMD 108 to provide single- or multiple-chamber pacing for cardiac therapy. FIG. 3 illustrates a configuration 200 of the system 100 including one example of an intracardiac IMD 202 in the heart 104. FIG. 4 illustrates a configuration 250 of the system 100 including one example of an intracardiac IMD 252 and one example of a leaded IMD 254. FIG. 5 illustrates a configuration 270 of the system 100 including one example of a leaded IMD 272.

As shown in FIG. 3, the configuration 200 may include an intracardiac IMD 202 having a housing 204 implantable, positioned, or disposed, in the RV 206 of the heart 104, a leadlet 208 coupled to the housing 204 extending from the RV 206 to the RA 210 through the tricuspid valve 212. The intracardiac IMD 202 may include a plurality of electrodes coupled to the intracardiac housing 204 or the leadlet 208. For example, the plurality of electrodes may include one or more of a ventricular electrode 214 (or LV electrode), an RA electrode 216 (or atrial electrode), an optional RV electrode 218, and an optional housing-based electrode 232 (or common electrode).

The ventricular electrode 214 may be used for sensing or pacing one of the ventricles, such as the LV 222 of the heart 104, to provide cardiac therapy. The ventricular electrode 214 may be coupled to the housing 204 or even another leadlet (not shown) extending from the housing 204. The ventricular electrode 214 may be implanted in the ventricular septum 220 of the heart 104. In particular, the ventricular electrode 214 may be implantable in the endocardium of the LV 222 in the ventricular septum 220, which may also be described as the LV septum. The ventricular electrode 214 may be implanted through the ventricular septum 220 in the RV 206, or RV septum, into the endocardium of the LV 222.

The RA electrode 216 may be used for sensing or pacing of the RA 210 of the heart 104 to deliver cardiac therapy to or sense electrical activity of the RA 210. The RA electrode 216 may be coupled to the leadlet 208. The RA electrode 216 may be implanted in the endocardium of the RA 210, which may facilitate low sensing or pacing thresholds. Alternatively, the RA electrode 216 may implanted to be free floating in the blood volume of the RA 210.

The RV electrode 218 may be used for sensing or pacing of the RV 206 of the heart 104 to provide cardiac therapy. The RV electrode 218 may be coupled to the housing 204 or even another leadlet (not shown) extending from the housing 204. The RV electrode 218 may be implanted in ventricular septum 220 of the heart 104. In particular, the RV electrode 218 may be implantable in the endocardium of the RV 206 in the ventricular septum 220, which may also be described as the RV septum.

The intracardiac IMD 202 may include a tissue-penetrating electrode assembly 224 to position one or more electrodes in cardiac tissue corresponding to the same or adjacent chamber of the heart 104. Any suitable shape may be used to form the tissue-penetrating electrode assembly 224 to position the ventricular electrode 214 and the optional RV electrode 218. For example, the tissue-penetrating electrode assembly 224 may include a helix shape or a dart shape.

The tissue-penetrating assembly 224 may be coupled to a distal end portion of the housing 204. The leadlet 208 may be coupled to the housing 204 on an opposite side (at a proximal end portion) from the tissue-penetrating electrode assembly 224.

The tissue-penetrating electrode assembly 224 may include the ventricular electrode 214 and the RV electrode 218. For example, the ventricular electrode 214 or the RV electrode 218 may be coupled to the housing 204 via the tissue-penetrating assembly 224. The tissue-penetrating electrode assembly 224 may be generally elongate and be used to be inserted through the RV septum to position the ventricular electrode 214 for pacing the LV septum. The RV electrode 218 may be disposed proximal to the ventricular electrode 214 along the tissue-penetrating electrode assembly 224.

In general, the tissue-penetrating electrode assembly 224 does not position, or deliver, the ventricular electrode 214 into the blood volume of the LV 222. For example, the length of the tissue-penetrating electrode assembly 224 may be sized to prevent penetration into the LV blood volume. In one example, the length of the tissue-penetrating electrode assembly 224 may be less than the width of the average ventricular septum.

The intracardiac IMD 202 may also include a fixation assembly to secure or attach the housing 204 or the leadlet 208 to tissue of the heart 104. For example, a tissue-penetrating electrode assembly 224 having a helix shape may be described as including or functioning as a fixation assembly. Alternatively, a fixation assembly may be formed separately from the tissue-penetrating assembly 224, such as separate hook-shaped tines.

The tissue-penetrating electrode assembly 224 may be implanted in various locations along the ventricular septum 220. In one example, as illustrated, the tissue-penetrating electrode assembly 224 may be implanted in the ventricular septum 220 proximate to the base 226, or basal portion, of the heart 104. Implantation proximate to the base 226 may allow for dual-bundle sensing and pacing, for example, by positioning the RV electrode 218 proximate to the right bundle branch and the ventricular electrode 214 proximate to the left bundle branch. In another example, the tissue-penetrating electrode assembly 224 may be implanted in the ventricular septum 220 proximate to the mid-septal portion of the heart 104. In a further example, the tissue-penetrating electrode assembly 224 may be implanted in the ventricular septum 220 proximate to the apex 230 of the heart 104. Implantation proximate to the apex 230 may facilitate use of a simple delivery system having fewer curves or changes in direction. In general, implantation in the ventricular septum 220 at any of these locations may be less complex than implantation in other septa of the heart 104 and may further facilitate sensing and pacing using relatively low thresholds compared to other implantation locations.

The intracardiac IMD 202 may also include a housing-based electrode 232. The housing-based electrode 232 may serve as a common reference for one or more of the other electrodes.

In general, this configuration 200 of the system 100 may be used to monitor electrical activity using one or both of the RA electrode 216 and the ventricular electrode 214 and may also be used to deliver cardiac therapy based on the monitored electrical activity, for example, using a controller contained in the housing 204. For example, this configuration 200 may be used to deliver three-chamber AV synchronous cardiac therapy or CRT for the RA 210, RV 206, and LV 222 using the RA electrode 216, the RV electrode 218, and the ventricular electrode 214, each operably coupled to the controller.

As shown in FIG. 4, the configuration 250 may include an intracardiac IMD 252 and a leaded IMD 254. The configuration 250 may have the same or similar structure or functionality as configuration 200 of FIG. 3, except that configuration 250 includes the leaded IMD 254 instead of a leadlet extending from the intracardiac IMD 252.

The intracardiac IMD 252 may be similar to the intracardiac IMD 202 described with respect to FIG. 3 except that the intracardiac IMD 252 does not include a leadlet. For example, the intracardiac IMD 252 may include one or more of the housing 204, the ventricular electrode 214, the RV electrode 218, the tissue-penetrating electrode assembly 224, and the housing-based electrode 232, as described with respect to the IMD 202 of FIG. 3. The intracardiac IMD 252 may be implanted in the ventricular septum 220 at any of the base 226, the mid-septal 228, or the apex 230 of the heart 104.

The leaded IMD 254 may include a housing 256 implantable, positioned, or disposed, in an extravascular location, an implantable medical lead 258 coupled to the housing 256 extending from the extravascular location to the RA 210 through the superior vena cava 260. The leaded IMD 254 may include one or more electrodes coupled to the housing 256 or the lead 258. For example, an RA electrode 216 and a housing-based electrode 264 coupled to the lead 258.

The RA electrode 216 may be implanted in the RA 210 of the heart 104. The housing-based electrode 264 may be used as a common reference electrode in addition to or as an alternative to housing-based electrode 232 on the intracardiac IMD 252.

In general, this configuration 250 of the system 100 may be used to monitor electrical activity and may also be used to deliver cardiac therapy based on the monitored electrical activity, for example, using a first controller contained in the housing 204 of the intracardiac IMD 252 and a second controller contained in the housing 256 of the leaded IMD 254. For example, the first controller of the intracardiac IMD 252 may be configured to wirelessly communicate with the second controller of leaded IMD 254 to monitor electrical activity using one or both of the RA electrode 216 and the ventricular electrode 214.

The controllers may be in operative communication with one another, for example, using a wireless communication interface or using a signaling pulse to carry out the monitoring of electrical activity and the delivery of cardiac therapy. For example, this configuration 250 may be used to deliver three-chamber AV synchronous cardiac therapy or CRT for the RA 210, RV 206, and LV 222 by using the RA electrode 216, the RV electrode 218, and the LV electrode 214, each operably coupled to the respective first or second controller in wireless communication with one another.

As shown in FIG. 5, the configuration 270 may include a leaded IMD 272. The configuration 270 may have the same or similar structure or functionality as configuration 250 of FIG. 4, except that configuration 270 includes a ventricular lead instead of an intracardiac IMD in the RV 206. In particular, the leaded IMD 272 is similar to leaded IMD 254 described with respect to FIG. 4 except that the leaded IMD 272 further includes a ventricular lead 274. For example, the leaded IMD 272 includes a housing 256, an implantable medical lead 258 (or RA lead), an RA electrode 216, and a housing-based electrode 264.

The leaded IMD 272 includes the ventricular lead 274, which may be coupled to the housing 256 and implantable in the ventricular septum 220. In particular, the ventricular lead 274 may extend through the superior vena cava 260, through the RA 210, through the tricuspid valve 212, and into the RV 206. The leaded IMD 254 may include one or more electrodes coupled to the housing 256 or the ventricular lead 274. For example, a ventricular electrode 214 may be coupled to the ventricular lead 274.

The leaded IMD 272 may include a tissue-penetrating electrode assembly 224 coupled to the ventricular lead 274 at a distal end portion of the leaded IMD 272. An RV electrode 218 may also be coupled to the tissue-penetrating electrode assembly 224. The tissue-penetrating electrode assembly 224 may be implanted in the ventricular septum 220 at any of the base 226, the mid-septal 228, or the apex 230 of the heart 104.

In general, this configuration 270 of the system 100 may be used to monitor electrical activity using one or both of the RA electrode 216 and the ventricular electrode 214 and may also be used to deliver cardiac therapy based on the monitored electrical activity, for example, using a controller contained in the housing 256. For example, this configuration 270 may be used to deliver three-chamber AV synchronous cardiac therapy or CRT for the RA 210, RV 206, and LV 222 using the RA electrode 216 coupled to the implantable medical lead 258 and the RV electrode 218 and the LV electrode 214 each coupled to the ventricular lead 274, each of the electrodes being operably coupled to the controller.

Figure 6:
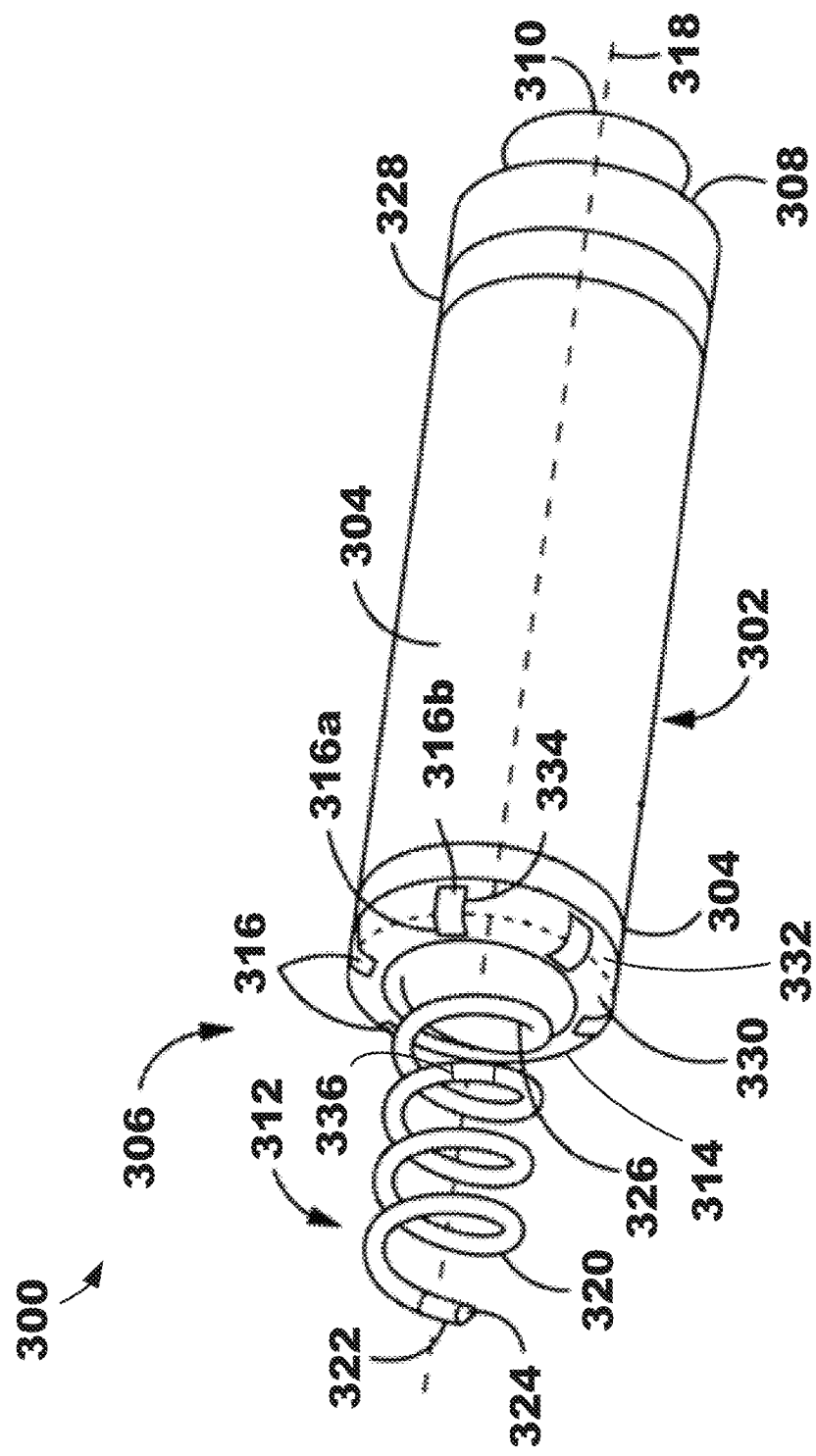
FIG. 6 is a perspective diagram that illustrates a first example of an intracardiac implantable medical device for use in the implantable medical system of FIG. 1.
Figure 7:
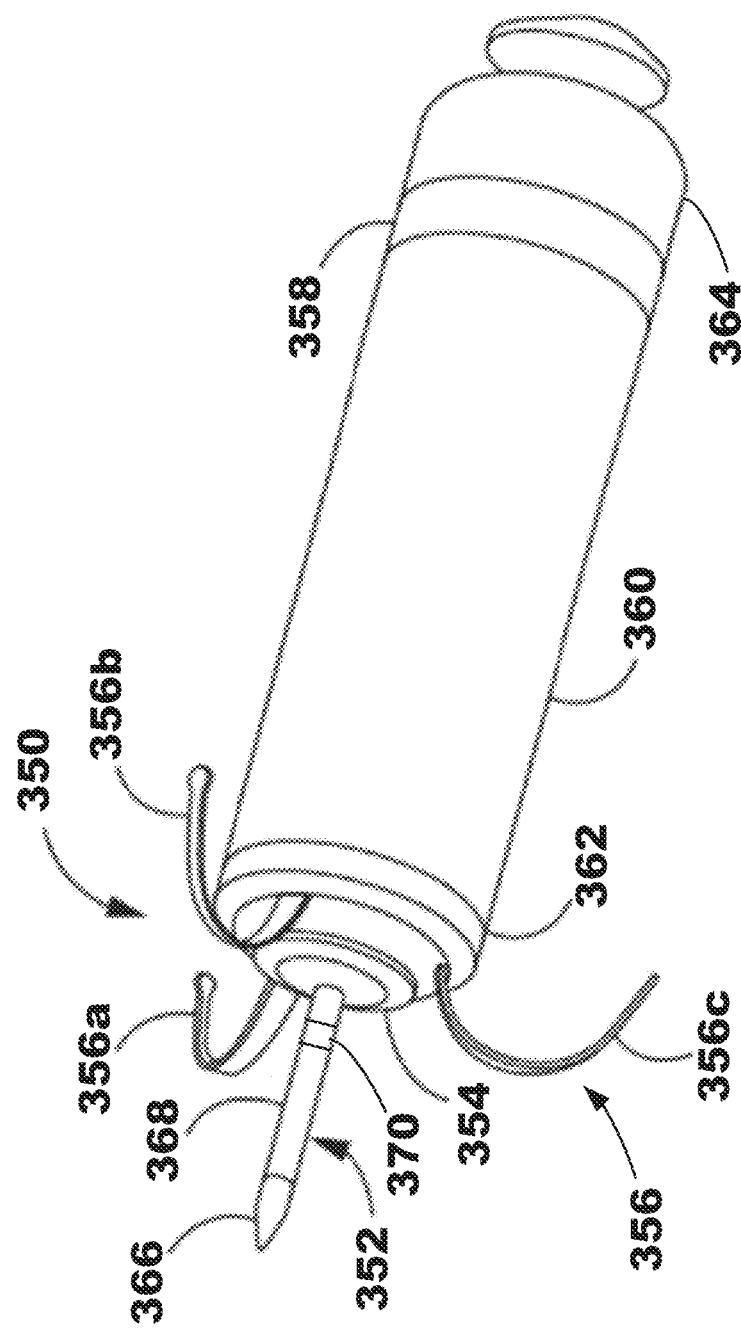
FIG. 7 is a perspective diagram that illustrates a second example of an intracardiac implantable medical device for use in the implantable medical system of FIG. 1.

FIGS. 6-7 show two examples of intracardiac IMDs that may be used in system 100 for implantation into the ventricular septum from the RV toward the LV to provide single- or multiple-chamber pacing for cardiac therapy. Although not shown in FIGS. 6-7, each of the intracardiac IMDs may include a leadlet, such as leadlet 208 (FIG. 3) coupled to a proximal end region 308 of the intracardiac housing 302 extending proximally to be implanted in the RA.

FIG. 6 shows a first example of an intracardiac IMD that may be used in system 100. An intracardiac IMD 300 may be configured to calibrate pacing therapy and/or deliver pacing therapy for single or multiple chamber cardiac therapy (e.g., dual- or triple-chamber cardiac therapy). The intracardiac IMD 300 may include a housing 302 having, or defining, an outer sidewall 304, shown as a cylindrical, outer sidewall, extending from a housing distal end region 306 to a housing proximal end region 308. The housing 302 may enclose electronic circuitry configured to perform single- or multiple-chamber cardiac therapy, including electrical signal sensing and pacing of the ventricular chambers. A delivery tool interface member 310 may be disposed on or proximate the housing proximal end region 308.

The intracardiac IMD 300 may include an electrically-insulative distal member 314 coupled to the housing distal end region 306. Multiple non-tissue piercing electrodes, or non-tissue penetrating electrodes, may be coupled directly to the insulative distal member 314.

A tissue-penetrating electrode assembly 312 may be coupled to the housing distal end region 306. The tissue-penetrating electrode assembly 312 may extend away from the housing distal end region 306. The tissue-penetrating electrode assembly 312 may be coaxial with a longitudinal center axis 318 extending along the elongate shape the housing 302.

The tissue-penetrating electrode assembly 312 may include or be integrated with a fixation assembly in the form of a helix. The tissue-penetrating electrode assembly 312 may be described as a helix electrode assembly.

The tissue-penetrating electrode assembly 312 may include an electrically insulated shaft 320 and one or more electrodes, such as a ventricular electrode 322 (LV electrode) and a ventricular electrode 336 (RV electrode), which may be described as tissue-piercing or tissue-penetrating electrodes. The ventricular electrode 322 may be described as a distal cathode ventricular electrode 322, and the ventricular electrode 336 may be described as a proximal cathode ventricular electrode 336.

The tissue-penetrating electrode assembly 312 may be described as an "active" fixation assembly. The tissue-penetrating electrode assembly 312 may include a helix-shaped, or helical, shaft 320. The helical shaft 320 may extend from a shaft distal end region 324 to a shaft proximal end region 326, which may be directly coupled to the insulative distal member 314. The helical shaft 320 may be coated with an electrically insulating material to avoid sensing or stimulation of cardiac tissue along the shaft length.

The ventricular electrode 322 may be disposed at or proximate to the shaft distal end region 324. The ventricular electrode 336 may be disposed proximal to the ventricular electrode 322 along the shaft 320 closer to the housing 302. In some cases, the ventricular electrode 336 is disposed at or proximate to the shaft proximal end region 324.

When using the IMD 300 as a pacemaker for multiple chamber pacing (e.g., dual or triple chamber pacing) and sensing, the ventricular electrode 322 may be used as a cathode electrode and the ventricular electrode 336 or the ventricular electrode 316 may be used as a cathode electrode (RV electrode) each paired with the proximal housing-based electrode 328 serving as a common return anode electrode. Alternatively, the ventricular electrode 336, the ventricular electrode 316, or the housing-based electrode 328 may serve as a return anode electrode paired with the ventricular electrode 322 (LV electrode) as a cathode for sensing LV signals and delivering LV pacing pulses.

The proximal housing-based electrode 328 may be a ring electrode circumscribing the housing 302 and may be defined by an uninsulated portion of the longitudinal outer sidewall 304. Other portions of the housing 302 not serving as an electrode may be coated with an electrically insulating material.

The ventricular electrode 316 may be described as a non-tissue piercing electrode. Multiple non-tissue piercing electrodes may be provided along a periphery of the insulative distal member 314, peripheral to the tissue-penetrating electrode assembly 312. The insulative distal member 314 may define a distal-facing surface 330 of the intracardiac IMD 300 and may define a circumferential surface 332 that circumscribes the intracardiac IMD 300 adjacent to the housing longitudinal sidewall 304. As illustrated, six non-tissue piercing electrodes may be spaced apart radially at equal distances along the outer periphery of insulative distal member 314. In general, one, two, or more non-tissue piercing electrodes may be provided.

When the ventricular electrode 322 is implanted and positioned in the LV myocardium in the ventricular septum (or LV septum), the ventricular electrode 336 may be implanted and positioned in the RV myocardium in the ventricular septum (or RV septum).

Alternatively, or additionally, when the ventricular electrode 322 is implanted and positioned in the LV myocardium, at least one ventricular electrode 316 may be positioned against, in intimate contact with, or in operative proximity to, an RV tissue surface for delivering pulses and/or sensing cardiac electrical signals produced by the patient's heart. For example, non-tissue piercing electrodes may be positioned in contact with RV endocardial tissue for pacing and sensing in the RV when the tissue-penetrating electrode assembly 312 is advanced into the RV septal tissue until the distal tip ventricular electrode 322 is positioned in direct contact with LV septal tissue, such as the LV myocardium and/or a portion of the ventricular conduction system.

By providing multiple non-tissue piercing electrodes along the periphery of the insulative distal member 314, the angle of the tissue-penetrating electrode assembly 312 and the housing distal end region 306 relative to the cardiac surface, e.g., the RV endocardial surface, may not be required to be substantially parallel.

The ventricular electrode 316 may be disposed in one or more recesses 334 to be subflush, flush, or raised relative to the housing 302. The non-tissue piercing electrodes are shown to each include a first portion 316a extending along the distal-facing surface 330 and a second portion 316b extending along the circumferential surface 332.

FIG. 7 shows a second example of an intracardiac IMD that may be used in the system 100. An intracardiac IMD 350 that may be configured for calibrating pacing therapy and/or delivering pacing therapy and include a tissue-penetrating electrode assembly 352. The intracardiac IMD 350 may have the same or similar functionality as the intracardiac IMD 300 of FIG. 6 except that intracardiac IMD 350 uses a different form of tissue-penetrating electrode assembly and distal housing-based electrode.

The tissue-penetrating electrode assembly 352 may include or be integrated with a fixation assembly in the form of a dart. The tissue-penetrating electrode assembly 352 may be described as a dart electrode assembly.

The intracardiac IMD 350 may include a housing 360. The housing 360 may define a hermetically sealed internal cavity in which internal components of the intracardiac IMD 350 reside, such as a sensing circuit, a therapy delivery circuit, a control circuit (or controller with processing circuitry), memory, communication interface (or telemetry circuit), other optional sensors, and a power source. The housing 360 may be described as extending between a distal end region 362 and a proximal end region 364 in a generally cylindrical shape to facilitate catheter delivery. Alternatively, the housing 360 may be any other shape to perform the functionality and utility described herein. The housing 360 may include a delivery tool interface member, e.g., at the proximal end region 364, for engaging with a delivery tool during implantation of the intracardiac IMD 350.

All or a portion of the housing 360 may function as an electrode during cardiac therapy, for example, in sensing and/or pacing. In the example shown, the housing-based electrode 358 is shown to circumscribe a proximal portion of the housing 360. When the housing 360 is formed from an electrically conductive material portions of the housing 360 may be electrically insulated by a non-conductive material leaving one or more discrete areas of conductive material exposed to define the proximal housing-based electrode 358. When the housing 360 is formed from a non-conductive material, an electrically conductive coating or layer may be applied to one or more discrete areas of the housing 30 to form the proximal housing-based electrode 24. In other examples, the proximal housing-based electrode 358 may be a component, such as a ring electrode, that is mounted or assembled onto the housing 360. The proximal housing-based electrode 358 may be electrically coupled to internal circuitry of the intracardiac IMD 350, e.g., via the electrically conductive housing 360 or an electrical conductor when the housing 360 is a non-conductive material. In the example shown, the proximal housing-based electrode 358 is located nearer to the housing proximal end region 364 than the housing distal end region 362.

The tissue-penetrating electrode assembly 352 may be disposed at the distal end region 362 of the intracardiac IMD 350. The tissue-penetrating electrode assembly 352 may include one or more electrodes, such as ventricular electrode 366 (or LV electrode) and ventricular electrode 370 (or RV electrode) coupled to one or more shafts 368, or darts, of equal or unequal length.

The shaft 368 may extend distally away from the housing distal end region 362. The ventricular electrode 366 may be disposed at or near the free, distal end region of the shaft 368. The ventricular electrode 366 may have a conical or hemi-spherical distal tip with a relatively narrow tip diameter (e.g., less than 1 mm) for penetrating into and through tissue layers without using a sharpened tip or needle-like tip having sharpened or beveled edges. The ventricular electrode 370 may be disposed proximal to the ventricular electrode 366 along the shaft 368 nearer to the housing 360. In particular, when the ventricular electrode 366 is implanted and positioned in the LV myocardium in the ventricular septum (or LV septum), the ventricular electrode 370 may be implanted and positioned in the RV myocardium in the ventricular septum (or RV septum).

The shaft 368 may be a normally straight member and may be rigid. Alternatively, the shaft 368 may be described as being relatively stiff but still possessing limited flexibility in lateral directions. Further, the shaft 368 may be non-rigid to allow some lateral flexing with heart motion. However, in a relaxed state, when not subjected to any external forces, the shaft 368 may maintain a straight position as shown to hold the ventricular electrode 366 spaced apart from the housing distal end region 362 at least by the longitudinal height of the shaft 368.

The tissue-penetrating electrode assembly 352 may be configured to pierce through one or more tissue layers to position the ventricular electrode 366 within a desired tissue layer, e.g., the ventricular myocardium. As such, the longitudinal height of the shaft 368 may correspond to the expected pacing site depth, and the shaft 368 may have a relatively high compressive strength along its longitudinal axis to resist bending in a lateral or radial direction when pressed against the implant region.

The intracardiac IMD 350 may include a fixation assembly separate from the tissue-penetrating electrode assembly 352. As illustrated, a fixation assembly 356 may be operably coupled to the housing 360 that is couplable to cardiac tissue, such as the RV endocardium. The fixation assembly 356 may include three fixation elements 356a, 356b, 356c are shown. The fixation elements may be described as "tines" having a normally curved position. The tines may be held in a distally extended position within a delivery tool. The distal tips of tines may penetrate the heart tissue to a limited depth before elastically curving back proximally into the normally curved position (shown) upon release from the delivery tool. Further, the fixation assembly 356 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference.

In some examples, the intracardiac IMD 350 includes a distal housing-based ventricular electrode 354 in addition to, or as an alternative to, the ventricular electrode 370. As illustrated, the ventricular electrode 354 may include a portion on a distal surface of the housing 360 or a portion on the circumferential outer surface of the housing 360.

When using the IMD 350 as a pacemaker for multiple chamber pacing (e.g., dual or triple chamber pacing) and sensing, the ventricular electrode 366 may be used as a cathode electrode and the ventricular electrode 354 or the ventricular electrode 370 may be used as a cathode electrode (RV electrode) each paired with the proximal housing-based electrode 358 serving as a common return anode electrode. Alternatively, the ventricular electrode 354, the ventricular electrode 370, or the housing-based electrode 358 may serve as a return anode electrode paired with the ventricular electrode 366 (LV electrode) as a cathode for sensing LV signals and delivering LV pacing pulses.

The tissue-penetrating electrode assembly 352 may define the longitudinal height of the shaft 368 for penetrating through the RV endocardium in the target implant region and into the LV myocardium without perforating through the ventricular endocardial surface into the LV blood volume. When the longitudinal height of the shaft 368 fully advances into the target implant region, the ventricular electrode 366 may rest within the LV myocardium, and the ventricular electrode 370 or the ventricular electrode 354 may be positioned in the RV myocardium or in intimate contact with or close proximity to the RV endocardium, respectively.

Figure 8:
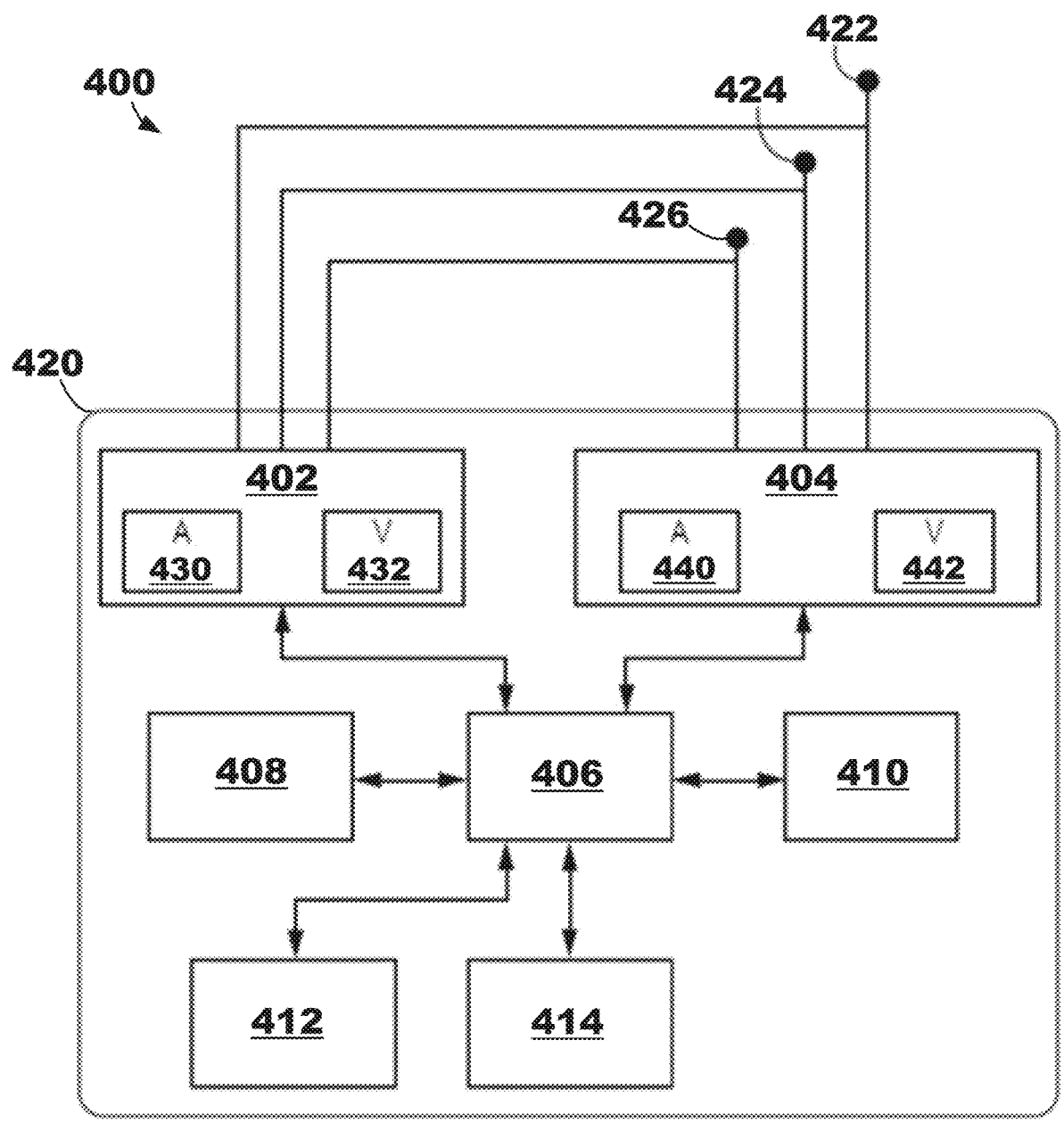
FIG. 8 is a schematic diagram that illustrates one example of an implantable medical device for use in the implantable medical system of FIG. 1.

FIG. 8 shows one example of a schematic layout of an IMD of the system 100, which may be used for one or more of the intracardiac IMD 106, the leaded IMD 108, or the extravascular IMD 110, for example, to provide single- or multiple-chamber pacing for cardiac therapy. As illustrated, the IMD 400 may include various components, such as a sensing circuit 402, a therapy delivery circuit 404, processing circuitry 406 (a control circuit or processor) operably coupled to the sensing and therapy delivery circuits, communication interface 408 (a telemetry circuit) operably coupled to the processing circuitry, memory 410 operably coupled to the processing circuitry, one or more other sensors 412 operably coupled to the processing circuitry, and a power source 414 operably coupled to the processing circuitry. One or more of these components may be contained within a housing 420.

In general, the memory 410 may be used to store parameters or other information or data that is predetermined, received, or determined by the processing circuitry 406 for later retrieval and use by other components of the IMD 400. The power source 414 may provide power to the circuitry of the IMD 400 including one or more of the components as needed. The power source 414 may include one or more energy storage devices, such as one or more rechargeable or non-rechargeable batteries.

The components of IMD 400 may cooperatively monitor atrial or ventricular electrical cardiac signals, determine when a cardiac therapy is necessary, and/or deliver electrical pulses to the patient's heart according to programmed therapy mode and pulse control parameters. In particular, the sensing circuit 402 may be operably coupled to one or more electrodes to monitor electrical activity of the heart in one or more of the LV, RV, and RA. For example, the sensing circuit 402 may be operably coupled to one or more of a first ventricular electrode 422 (LV electrode), a second ventricular electrode 424 (RV electrode), and an atrial electrode 426 (RA electrode). The sensing circuit 402 may also be operably coupled to a common reference electrode (not shown), such as a housing-based electrode.

The sensing circuit 402 may include one or both of an atrial sensing channel 430 and a ventricular sensing channel 432. The atrial electrode 426 may be operably coupled to the atrial sensing channel 430. The first ventricular electrode 422 or the second ventricular electrode 424 may be operably coupled to the ventricular sensing channel 432. A housing-based electrode may be operably coupled to the ventricular sensing channel 432.

The therapy delivery circuit 404 may be operably coupled to one or more electrodes to deliver cardiac therapy, such as CRT, to one or more chambers of the heart, such as the LV, RV, and RA. For example, the therapy delivery circuit 404 may be operably coupled to one or more of a first ventricular electrode 422 (LV electrode), a second ventricular electrode 424 (RV electrode), and a atrial electrode 426 (RA electrode). The therapy delivery circuit 404 may also be operably coupled to a common reference electrode (not shown), such as a housing-based electrode.

The therapy delivery circuit 404 may include one or both of an atrial pacing channel 440 and a ventricular pacing channel 442. The atrial electrode 426 may be operably coupled to the atrial pacing channel 440. The first ventricular electrode 422 or the second ventricular electrode 424 may be operably coupled to the ventricular pacing channel 442. A housing-based electrode may be operably coupled to the ventricular pacing channel 442. The therapy delivery circuit 404 may also be used to deliver communication signals in the form of a pacing signal, for example, from an extravascular IMD to an intracardiac IMD.

In general, the IMD 400 may be configured to deliver one or more types of cardiac therapy, such as bradycardia pacing, CRT, post-shock pacing, and/or tachycardia-related therapy, such as ATP, among others. Each of the atrial sensing channel 430 and the ventricular sensing channel 432 may include cardiac event detection circuitry for detecting P-waves and R-waves, respectively, from the cardiac electrical signals received by the respective sensing channels. The cardiac event detection circuitry may be configured to amplify, filter, digitize, and rectify the cardiac electrical signal received from one or more selectable electrodes to improve the signal quality for detecting cardiac electrical events. The cardiac event detection circuitry may include one or more sense amplifiers, filters, rectifiers, threshold detectors, comparators, analog-to-digital converters (ADCs), timers, or other analog or digital components. A cardiac event sensing threshold, such as a P-wave sensing threshold and an R-wave sensing threshold, may be automatically adjusted by each respective sensing channel under the control of the processing circuitry 406, for example, based on timing intervals and sensing threshold values determined by the processing circuitry 406 or stored in the memory 410.

Upon detecting a cardiac electrical event based on a sensing threshold crossing, the sensing circuit 402 may produce a sensed event signal that is passed to the processing circuitry 406. For example, the atrial sensing channel 430 may produce a P-wave sensed event signal in response to a P-wave sensing threshold crossing. The ventricular sensing channel 432 may produce an R-wave sensed event signal in response to an R-wave sensing threshold crossing. The sensed event signals may be used by the processing circuitry 406 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 430 may cause the processing circuitry 406 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the processing circuitry 406 receives an R-wave sensed event signal from the ventricular sensing channel 432, the processing circuitry 406 may use the therapy delivery circuit 404 to deliver the scheduled ventricular pacing pulse synchronized to the sensed P-wave.

The atrial pacing channel 440 and the ventricular pacing channel 442 of the therapy delivery circuit 404 may each include charging circuitry, one or more charge storage devices, such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits. The ventricular pacing channel 442 may deliver ventricular pacing pulses, for example, upon expiration of an AV or VV pacing interval set by the processing circuitry 406 for providing atrial-synchronized ventricular pacing.

The atrial pacing channel 440 may be configured to deliver atrial pacing pulses. The processing circuitry 406 may set one or more atrial pacing intervals rate. The atrial pacing channel 440 may be controlled to deliver an atrial pacing pulse, for example, if an atrial pacing interval expires before a P-wave sensed event signal is received from the atrial sensing channel. The processing circuitry 406 may start an AV pacing interval in response to a delivered atrial pacing pulse to provide synchronized multiple-chamber pacing (e.g., dual- or triple-chamber pacing).

The IMD 400 may include other sensors 412 for sensing information about the patient for use in controlling electrical stimulation therapies delivered by the therapy delivery circuit 404. For example, a sensor indicative of a need for increased cardiac output may include a patient activity sensor, such as an inertial measurement unit (IMU) or accelerometer to measure motion. In general, information from the one or more other sensors 412 may be correlated to a physiological function, state, or condition of the patient, such as a patient activity sensor, for use in controlling cardiac therapy.

The communication interface 408 may be used to communicate with other devices in the system 100. The communication interface 408 may also be used for receiving parameters to program the processing circuitry 406, which may be stored as data in the memory 410. The communication interface 408 may include a transceiver and antenna for wirelessly communicating with an external device using radio frequency (RF) communication or other communication protocols. The communication interface 408 may be configured to be unidirectional or bi-directional.

Figure 9:
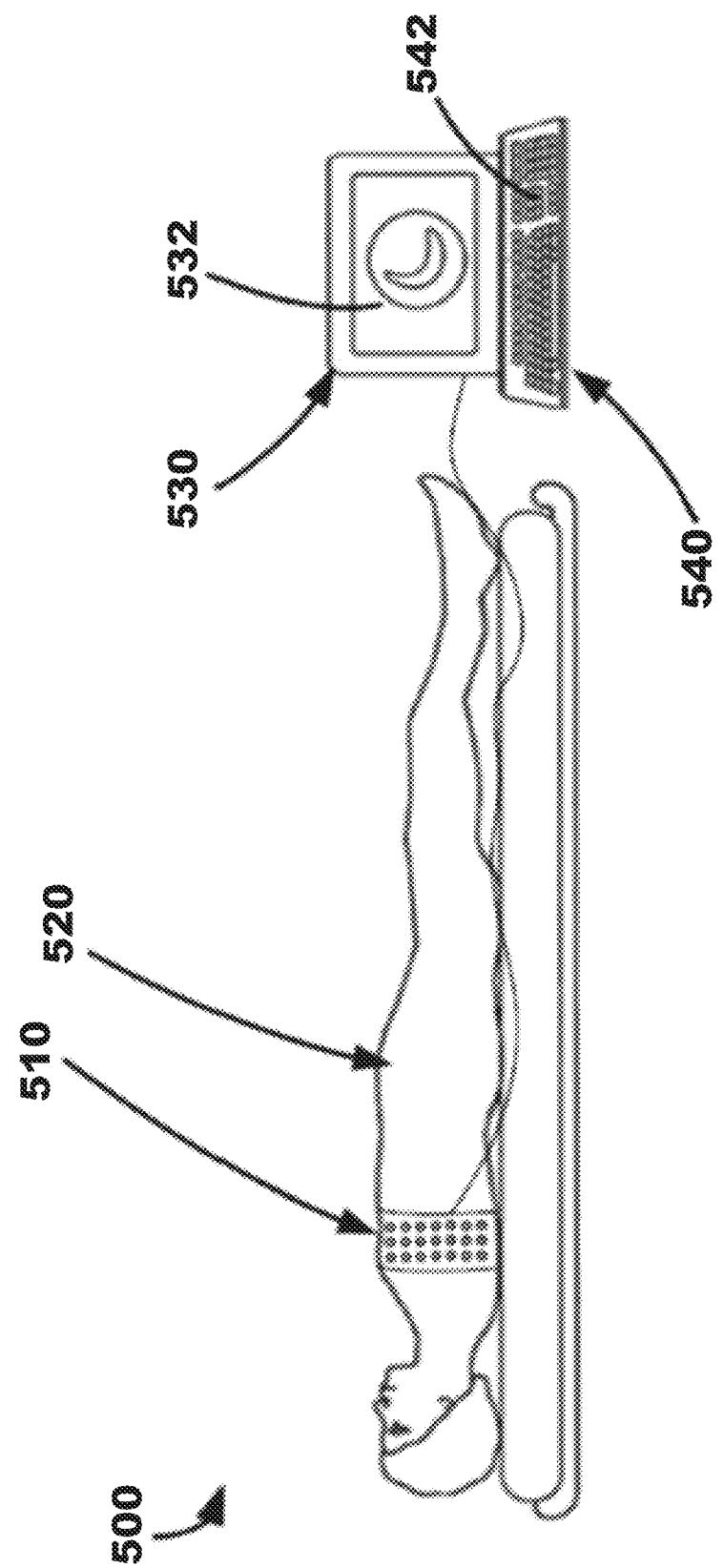
FIG. 9 is a diagram of an external apparatus including electrode apparatus, display apparatus, and computing apparatus for use in the implantable medical systems and devices of FIGS. 1-8.
Figure 10:
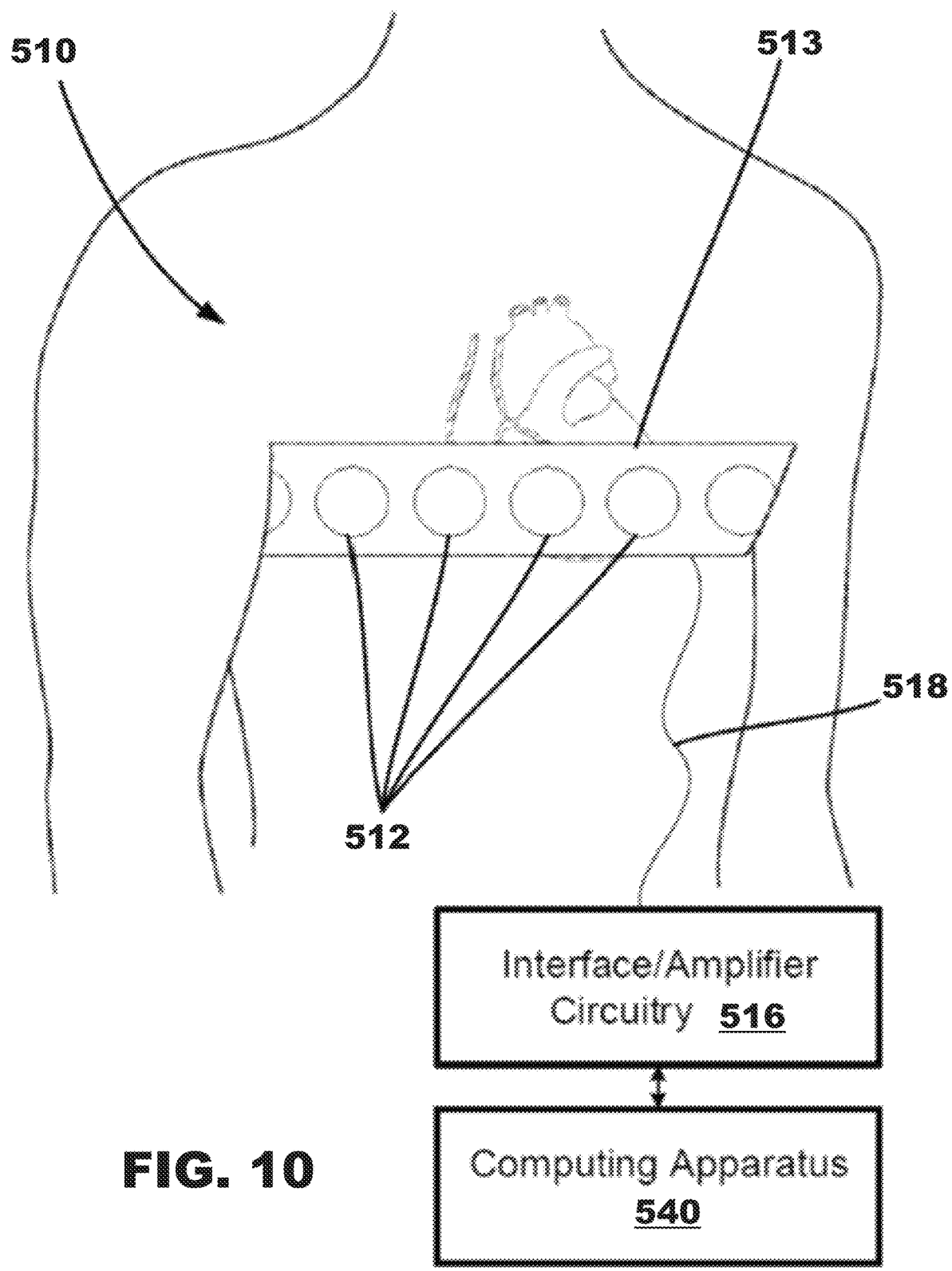
FIGS. 10-11 are diagrams of two examples of external electrode apparatus for measuring torso-surface potentials for use in the external apparatus of FIG. 9.
Figure 11:
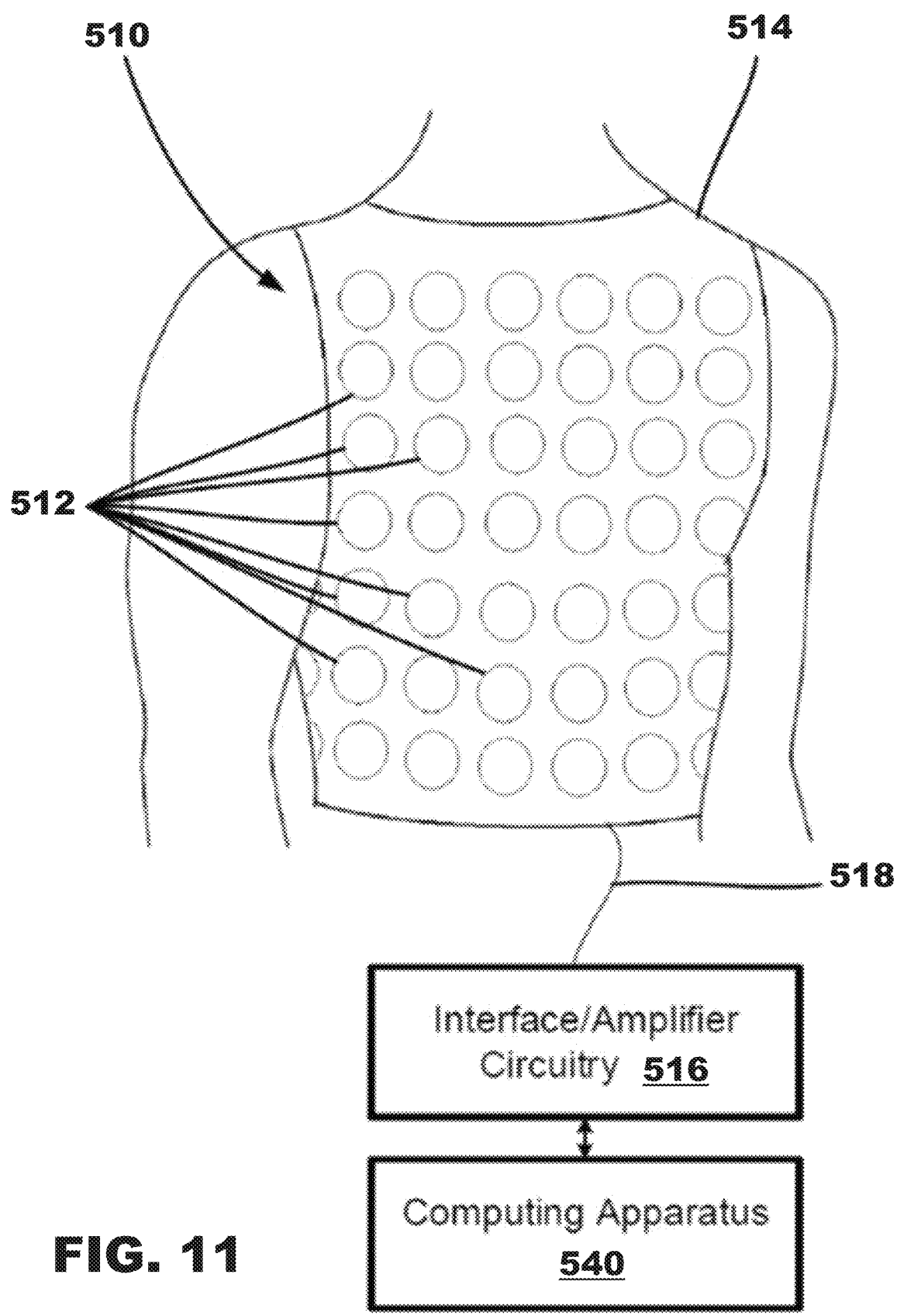

FIGS. 9-11 show examples of external apparatus may be used to facilitate implantation or configuration of the system 100. FIG. 9 depicts one example of a system 500 of the external apparatus including electrode apparatus 510, display apparatus 530, and computing apparatus 540.

The electrode apparatus 510 as shown includes a plurality of electrodes incorporated, or included, within a band wrapped around the chest, or torso, of a patient 520. The electrode apparatus 510 is operatively coupled to the computing apparatus 540 (e.g., through one or wired electrical connections, wirelessly, etc.) to provide electrical signals from each of the electrodes to the computing apparatus 540 for analysis, evaluation, etc. Electrode apparatus may be described in U.S. Pat. No. 9,320,446 entitled "Bioelectric Sensor Device and Methods" and issued on Apr. 26, 2016, which is incorporated herein by reference in its entirety.

Although not described herein, the system 500 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools, such as contrast solution. It is to be understood that the systems, methods, and interfaces described herein may further use imaging apparatus to provide noninvasive assistance to a user (e.g., a physician) to calibrate and/or deliver a cardiac pacing therapy, to locate and position a device to deliver cardiac pacing therapy, and/or to locate or select a pacing electrode or pacing vector proximate the patient's heart for cardiac pacing therapy in conjunction with the evaluation of cardiac pacing therapy.

For example, the systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a paced setting is optimal or determining whether one or more selected parameters are optimal, such as selected location information (e.g., location information for the electrodes to target a particular location in the left ventricle). Systems and methods that use imaging apparatus and/or electrode apparatus may be described in U.S. Pat. No. 9,877,789 issued on Jan. 30, 2018, and entitled "Implantable Electrode Location Selection," U.S. Pat. No. 10,251,555 issued Apr. 9, 2019, and entitled "Implantable Electrode Location Selection," U.S. Pat. No. 9,924,884 issued on Mar. 27, 2018, and entitled "Systems, Methods, and Interfaces for Identifying Effective Electrodes," U.S. Pat. No. 10,064,567 issued on Sep. 4, 2018, and entitled "Systems, Methods, and Interfaces for Identifying Optical-Electrical Vectors," each of which is incorporated herein by reference in its entirety.

Imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MM), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MM, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the RV or LV) within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 issued May 20, 2014, to Zarkh et al. U.S. Pat. No. 8,861,830 issued Oct. 14, 2014, to Brada et al., U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 530 and the computing apparatus 540 may be configured to display and analyze data such as, e.g., electrical signals (e.g., electrocardiogram data), cardiac information representative of one or more of mechanical cardiac functionality and electrical cardiac functionality (e.g., mechanical cardiac functionality only, electrical cardiac functionality only, or both mechanical cardiac functionality and electrical cardiac functionality), etc. Cardiac information may include, e.g., electrical heterogeneity information or electrical dyssynchrony information, surrogate electrical activation information or data, etc. that is generated using electrical signals gathered, monitored, or collected, using the electrode apparatus 510. The computing apparatus 540 may be a server, a personal computer, or a tablet computer. The computing apparatus 540 may be configured to receive input from input apparatus 542 and transmit output to the display apparatus 530. Further, the computing apparatus 540 may include data storage that may allow for access to processing programs or routines and/or one or more other types of data, e.g., for calibrating and/or delivering pacing therapy for driving a graphical user interface configured to noninvasively assist a user in targeting placement of a pacing device, and/or for evaluating pacing therapy at that location (e.g., the location of an implantable electrode used for pacing, the location of pacing therapy delivered by a particular pacing vector, etc.).

The computing apparatus 540 may be operatively coupled to the input apparatus 542 and the display apparatus 530 to, e.g., transmit data to and from each of the input apparatus 542 and the display apparatus 530. For example, the computing apparatus 540 may be electrically coupled to each of the input apparatus 542 and the display apparatus 530 using, e.g., analog electrical connections, digital electrical connections, wireless connections, bus-based connections, network-based connections, internet-based connections, etc. As described further herein, a user may provide input to the input apparatus 542 to manipulate, or modify, one or more graphical depictions displayed on the display apparatus 530 and to view and/or select one or more pieces of information related to the cardiac therapy.

Although as depicted the input apparatus 542 is a keyboard, it is to be understood that the input apparatus 542 may include any apparatus capable of providing input to the computing apparatus 540 for performing the functionality, methods, and/or logic described herein. For example, the input apparatus 542 may include a mouse, a trackball, a touchscreen (e.g., capacitive touchscreen, a resistive touchscreen, a multi-touch touchscreen, etc.), etc. Likewise, the display apparatus 530 may include any apparatus capable of displaying information to a user, such as a graphical user interface 532 including cardiac information, textual instructions, graphical depictions of electrical activation information, graphical depictions of anatomy of a human heart, images or graphical depictions of the patient's heart, graphical depictions of a leadless pacing device used to calibrate and/or deliver pacing therapy, graphical depictions of a leadless pacing device being positioned or placed to provide cardiac pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 530 may include a liquid crystal display, an organic light-emitting diode screen, a touchscreen, a cathode ray tube display, etc.

The processing programs or routines stored and/or executed by the computing apparatus 540 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more methods and/or processes described herein. Data stored and/or used by the computing apparatus 540 may include, for example, electrical signal/waveform data from the electrode apparatus 510, dispersions signals, windowed dispersions signals, parts or portions of various signals, electrical activation times from the electrode apparatus 510, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

Electrical activation times of the patient's heart may be useful to evaluate a patient's cardiac condition and/or to calibrate, deliver, or evaluate cardiac therapy to be or being delivered to a patient. Surrogate electrical activation information or data of one or more regions of a patient's heart may be monitored, or determined, using electrode apparatus 510 as shown in FIGS. 9-11. The electrode apparatus 510 may be configured to measure body-surface potentials of a patient 520 and, more particularly, torso-surface potentials of the patient 520.

As shown in FIG. 10, the electrode apparatus 510 may include a set, or array, of electrodes 512, a strap 513, and interface/amplifier circuitry 516. A portion of the set of electrodes may be used wherein the portion corresponds to a particular location on the patient's heart. The electrodes 512 may be attached, or coupled, to the strap 513, and the strap 513 may be configured to be wrapped around the torso of a patient 520 such that the electrodes 512 surround the patient's heart. As further illustrated, the electrodes 512 may be positioned around the circumference of a patient 520, including the posterior, lateral, posterolateral, anterolateral, and anterior locations of the torso of a patient 520.

Further, the electrodes 512 may be electrically connected to interface/amplifier circuitry 516 via wired connection 518. The interface/amplifier circuitry 516 may be configured to amplify the signals from the electrodes 512 and provide the signals to the computing apparatus 540. Other systems may use a wireless connection to transmit the signals sensed by electrodes 512 to the interface/amplifier circuitry 516 and, in turn, the computing apparatus 540, e.g., as channels of data. For example, the interface/amplifier circuitry 516 may be electrically coupled to each of the computing apparatus 540 and the display apparatus 530 using, e.g., analog electrical connections, digital electrical connections, wireless connections, bus-based connections, network-based connections, internet-based connections, etc.

Although in the example of FIG. 10 the electrode apparatus 510 includes a strap 513, in other examples any of a variety of mechanisms, e.g., tape or adhesives, may be employed to aid in the spacing and placement of electrodes 512. In some examples, the strap 513 may include an elastic band, strip of tape, or cloth. In other examples, the electrodes 512 may be placed individually on the torso of a patient 520. Further, in other examples, electrodes 512 (e.g., arranged in an array) may be part of, or located within, patches, vests, and/or other manners of securing the electrodes 512 to the torso of the patient 520.

The electrodes 512 may be configured to surround the heart of the patient 520 and record, or monitor, the electrical signals associated with the depolarization and repolarization of the heart after the signals have propagated through the torso of a patient 520. Each of the electrodes 512 may be used in a unipolar configuration to sense the torso-surface potentials that reflect the cardiac signals. The interface/amplifier circuitry 516 may also be coupled to a return or indifferent electrode (not shown) that may be used in combination with each electrode 512 for unipolar sensing. In some examples, there may be about 12 to about 50 electrodes 512 spatially distributed around the torso of the patient. Other configurations may have more or fewer electrodes 512.

The computing apparatus 540 may record and analyze the electrical activity (e.g., torso-surface potential signals)

sensed by electrodes 512 and amplified/conditioned by the interface/amplifier circuitry 516. The computing apparatus 540 may be configured to analyze the signals from the electrodes 512 to provide as anterior and posterior electrode signals and surrogate cardiac electrical activation times, e.g., representative of actual, or local, electrical activation times of one or more regions of the patient's heart as will be further described herein. The computing apparatus 540 may be configured to analyze the signals from the electrodes 512 to provide as anterior-septal electrode signals and surrogate cardiac electrical activation times, e.g., representative of actual, or local, electrical activation times of one or more anterior-septal regions of the patient's heart, as will be further described herein, e.g., for use in calibrating, delivering, and/or evaluating pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. Measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 540 may be configured to provide graphical user interfaces depicting the surrogate electrical activation times obtained using the electrode apparatus 510. Systems, methods, and/or interfaces may noninvasively use the electrical information collected using the electrode apparatus 510 to evaluate a patient's cardiac condition and/or to calibrate, deliver, or evaluate cardiac pacing therapy to be or being delivered to the patient.

FIG. 11 illustrates another electrode apparatus 510 that includes a plurality of electrodes 512 configured to surround the heart of the patient 520 and record, or monitor, the electrical signals associated with the depolarization and repolarization of the heart after the signals have propagated through the torso of the patient 520. The electrode apparatus 510 may include a vest 514 upon which the plurality of electrodes 512 may be attached, or to which the electrodes 512 may be coupled. The plurality, or array, of electrodes 512 may be used to collect electrical information such as, e.g., surrogate electrical activation times.

Similar to the electrode apparatus 510 of FIG. 10, the electrode apparatus 510 of FIG. 11 may include interface/amplifier circuitry 516 electrically coupled to each of the electrodes 512 through a wired connection 518 and be configured to transmit signals from the electrodes 512 to computing apparatus 540. As illustrated, the electrodes 512 may be distributed over the torso of a patient 520, including, for example, the anterior, lateral, posterolateral, anterolateral, and posterior surfaces of the torso of the patient 520.

The vest 514 may be formed of fabric with the electrodes 512 attached to the fabric. The vest 514 may be configured to maintain the position and spacing of electrodes 512 on the torso of the patient 520. Further, the vest 514 may be marked to assist in determining the location of the electrodes 512 on the surface of the torso of the patient 520. The vest 514 may include about 17 or more anterior electrodes positionable proximate the anterior torso of the patient, and about 39 or more posterior electrodes positionable proximate the posterior torso of the patient. In some examples, there may be about 25 electrodes 512 to about 256 electrodes 512 distributed around the torso of the patient 520, though other configurations may have more or fewer electrodes 512.

As described herein, the electrode apparatus 510 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 512, and not the entire set, can be used to generate activation times corresponding to a particular location of the patient's heart that the portion of the set of electrodes corresponds to.

The systems, methods, and interfaces may be used to provide noninvasive assistance to a user in the evaluation of a patient's cardiac health or status, and/or the evaluation of cardiac therapy such as CRT by use of the electrode apparatus 510 (e.g., cardiac therapy being presently-delivered to a patient during implantation or after implantation). Further, the systems, methods, and interfaces may be used to assist a user in the configuration, or calibration, of the cardiac therapy, such as CRT, to be or being delivered to a patient.

Electrical activity may be monitored using a plurality of external electrodes, such as electrodes 512 of FIGS. 9-11. The electrical activity can be monitored by a plurality of electrodes during pacing therapy or in the absence of pacing therapy. The monitored electrical activity can be used to evaluate pacing therapy to a patient. The electrical activity monitored using the ECG belt described can be used to evaluate at least one paced setting of the pacing therapy on the heart. As an example, a paced setting can be any one parameter or a combination of parameters including, but not limited to, electrode position, pacing polarity, pacing output, pacing pulse width, timing at which ventricular pacing is delivered relative to atrial timing, pacing rate, etc. Further, as an example, the location of the leadless device or a pacing lead can include a location in the right ventricle, left ventricle, or right atrium.

Further, body-surface isochronal maps of ventricular activation can be constructed using the monitored electrical activity during pacing therapy or in the absence of pacing therapy. The monitored electrical activity and/or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of pacing therapy at one or more paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In another example, only ASAT may be determined and further used, and/or ASAT may be more heavily weighted than other values.

One or more paced settings associated with the pacing therapy may be evaluated. A paced setting can include a plurality of pacing parameters. The plurality of pacing parameters can be optimal if the patient's cardiac condition improves, if the pacing therapy is effectively capturing a desired portion of the RA, RV, or LV, and/or if a metric of electrical heterogeneity improves by a certain threshold compared to a baseline rhythm or therapy. The determination of whether the paced setting is optimal can be based on at least one metric of electrical heterogeneity generated from electrical activity during pacing (and also, in some cases, during native conduction, or in the absence of pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, and/or if the location of the pacing therapy to excite the left ventricle causes a particular pattern of excitation of the muscle fibers in the heart. In addition, the plurality of pacing parameters can be optimal if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is optimal. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is may be optimal.

The paced setting can be determined to be optimal in response to the pacing therapy using the paced setting being acceptable, being beneficial, being indicative of complete engagement of patient's native cardiac conduction system, being indicative of correction of a ventricular conduction disorder (e.g., left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the pacing therapy, etc. The pacing location can refer to the location of any of the one or more pacing electrodes that are positioned using a lead, a leadless device, and/or any device or apparatus configured to deliver pacing therapy.

A paced setting for therapy may be adjusted. The paced setting can be adjusted in response to the paced setting being not optimal. The paced setting can be adjusted in response to the paced setting being within an optimal range but in order to determine whether the paced setting can be at a position within the optimal range that is more beneficial, more useful, more functional, etc., for the pacing therapy. The paced setting could be adjusted to find the most optimal metric of electrical heterogeneity.

A determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

Figure 12:
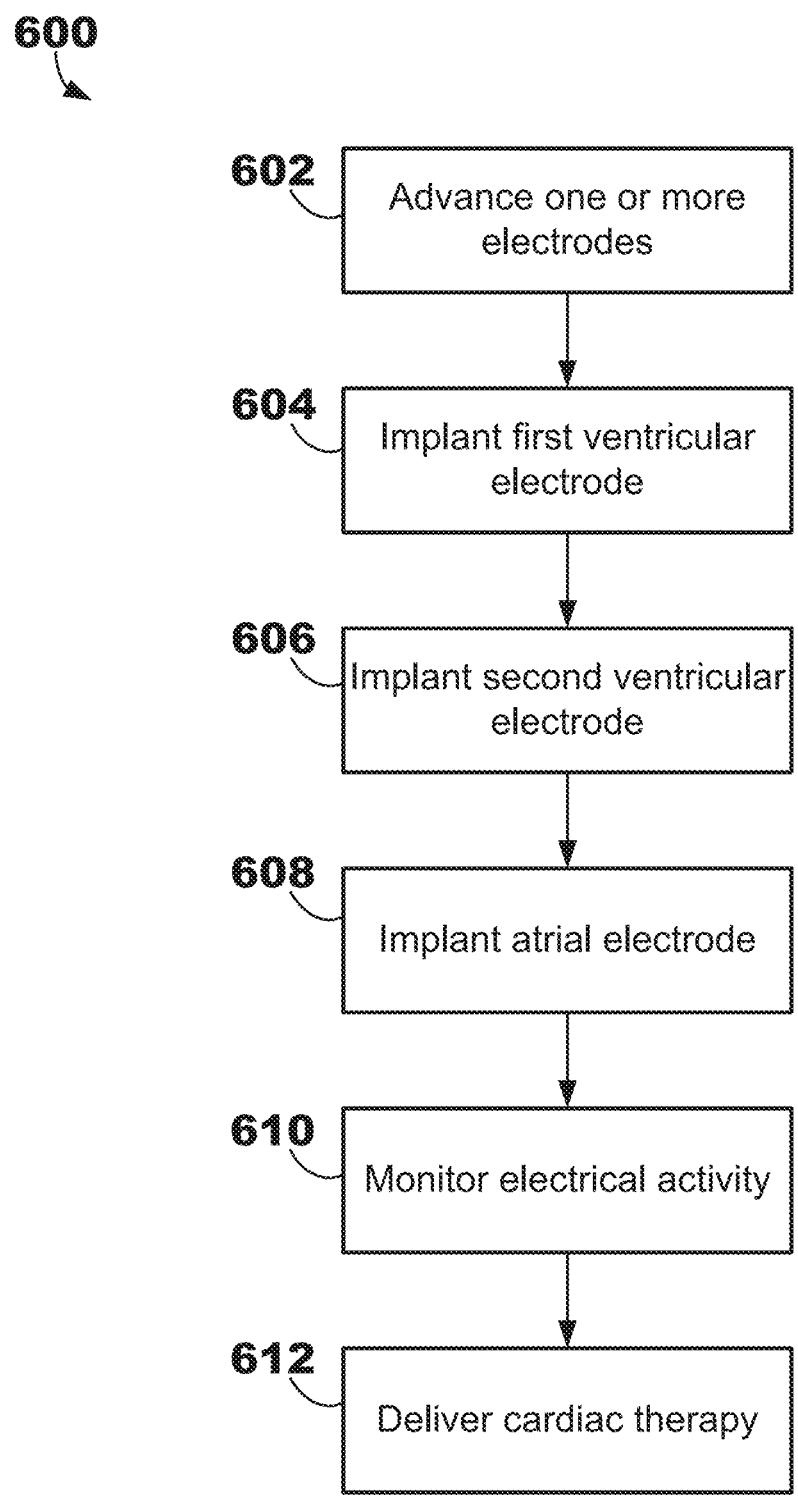
FIG. 12 is a flow diagram of one example of a method for providing cardiac therapy to a patient for use with, for example, the implantable medical systems, devices, and apparatus of FIGS. 1-11.

FIG. 12 shows one example of a method for use with the system 100 to provide cardiac therapy, such as CRT. The method 600 may include advancing one or more electrodes toward an implant location 602. In one example, one or more electrodes may be advanced along a path through the superior vena cava (SVC) of the patient. The one or more electrodes may be coupled to an intracardiac IMD or leaded IMD, such as described herein with respect to FIGS. 1-8.

The method 600 may also include implanting a first ventricular electrode 604 of the one or more electrodes. The first ventricular electrode may be an LV electrode, which may be implanted through the RV septum into the myocardium of the LV septum.

A second ventricular electrode of the one or more electrodes may also be implanted 606. The second ventricular electrode may be an RV electrode, which may be implanted into the myocardium of the RV septum or positioned in contact with the endocardium of the RV septum. The first and second ventricular electrodes may be used to monitor the electrical activity of or to deliver cardiac therapy to one or both ventricles.

The method 600 may also include implanting an atrial electrode 608 of the one or more electrodes. The atrial electrode may be an RA electrode, which may be implanted into the myocardium of the RA or positioned in contact with the endocardium of the RA. The RA electrode may be operably coupled to the same device, or a different device, as one or both of the ventricular electrodes.

After one or more electrodes are initially positioned, electrical activity may be monitored 610. For example, the atrial electrode may be used to monitor electrical activity of the RA, and the ventricular electrodes may be used to monitor electrical activity of one or both of the LV and the RV for use in delivering and/or adjusting cardiac therapy.

The method 600 may include delivering cardiac therapy 612. Cardiac therapy may be delivered based on, or in response to, the monitored electrical activity 610 using the one or more electrodes. For example, AV synchronous pacing may be delivered to the RA, RV, and LV using the RA electrode, RV electrode, and LV electrode, respectively.

Figure 13:
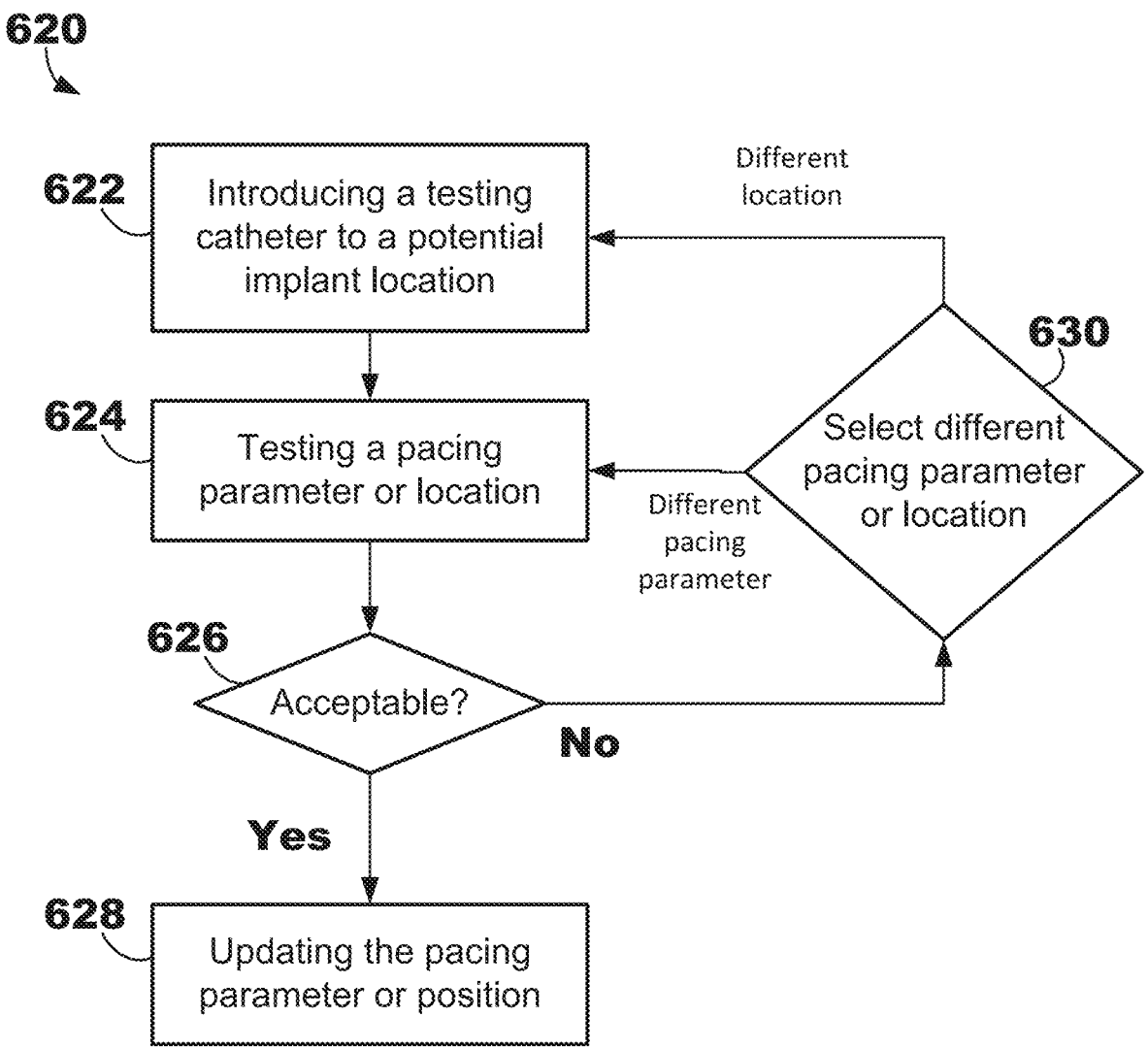
FIG. 13 is a flow diagram of one example of a method for determining an implant location for use with, for example, the implantable medical systems of FIGS. 1-8.

FIG. 13 shows one example of a method for use with the system 100 to determine one or more implant locations for one or more of the electrodes. The method 620 may include introducing a testing catheter to a potential implant location 622. The testing catheter may be operably coupled to a testing device capable of monitoring electrical activity and delivering test pulses. Any suitable testing catheter and testing device may be used, such as one known to one skilled in the art having the benefit of this disclosure.

The testing catheter may include a testing electrode. The testing electrode may be introduced along a retrograde path through the aorta of the patient to the LV. In particular, the testing electrode may be inserted into the myocardium of the LV septum to test one or more locations. The testing catheter may be moved to different positions along the ventricular septal wall to test more than one location. For example, locations along the LV septum proximate to the base, mid-septal, and apex may be tested. Using the aorta for testing LV pacing location in the LV septum may be faster than testing using an electrode that penetrates through the RV septum into the LV septum.

The method 620 may also include testing a pacing parameter or potential implant location 624. More than one location may be evaluated. A pacing parameter or location may be tested based on electrical activity, such as EHI, provided by using an external electrode apparatus having a plurality of external electrodes, such as described herein with respect to FIGS. 9-11.

The method 620 may include determining whether the pacing parameter or location is acceptable 626, for example, based on evaluating EHI that was generated from electrical activity monitored during delivery of the pacing using the pacing parameter or location. One or more pacing parameters or locations may also be compared to one another, and an optimal pacing parameter or location may be selected.

If the pacing parameter or location is not acceptable, the method 620 may include selecting a different pacing parameter or location 630. If a different location is selected, the method 620 may return to introduce the testing catheter at a new potential implant location 622 and test the same or different pacing parameter at the new potential implant location. If a different pacing parameter is selected, the method 620 may return to testing the different pacing parameter 624 at the same location.

If the pacing parameter or location is acceptable, the method 620 may update the pacing parameter or location 628, respectively. In particular, the particular pacing parameter or location may be noted, or stored in data, and the testing catheter may be removed. Method 600 of FIG. 12 may follow method 620. In particular, one or more electrodes may be implanted through the SVC based on the updated pacing parameter or location determined in method 620.

ILLUSTRATIVE EMBODIMENTS

While the present disclosure is not so limited, an appreciation of various aspects of the disclosure will be gained through a discussion of the specific illustrative embodiments provided below. Various modifications of the illustrative embodiments, as well as additional embodiments of the disclosure, will become apparent herein.

In embodiment A1, a leadless implantable medical device for a patient's heart includes:
  an intracardiac housing implantable in the right ventricle of the patient's heart;
  a leadlet coupled to the intracardiac housing extendable through the tricuspid valve of the patient's heart into the right atrium of the patient's heart;
  a plurality of electrodes coupled to one or both of the intracardiac housing and the leadlet, the plurality of electrodes including:
    a ventricular electrode implantable in the ventricular septal wall of the patient's heart to deliver cardiac therapy to or sense electrical activity of the left ventricle of the patient's heart; and
    a right atrial electrode coupled to the leadlet and implantable to deliver cardiac therapy to or sense electrical activity of the right atrium of the patient's heart;
  a therapy delivery circuit operably coupled to the plurality of electrodes to deliver cardiac therapy to the patient's heart;
  a sensing circuit operably coupled to the plurality of electrodes to sense electrical activity of the patient's heart; and
  a controller including processing circuitry operably coupled to the therapy delivery circuit and the sensing circuit, the controller configured to:
    monitor electrical activity using one or both of the right atrial electrode and the ventricular electrode; and
    deliver cardiac therapy based on the monitored electrical activity.

In embodiment A2, a device includes the device according to embodiment A1, wherein delivering cardiac therapy includes delivering cardiac resynchronization therapy.

In embodiment A3, a device includes the device according to embodiment A1 or A2, wherein the plurality of electrodes further includes a right ventricular electrode implantable in the right ventricle of the patient's heart to deliver cardiac therapy to or sense electrical activity of the right ventricle.

In embodiment A4, a device includes the device according to embodiment A3, further including a tissue-penetrating electrode assembly including the right ventricular electrode and the ventricular electrode distal to the right ventricular electrode.

In embodiment A5, a device includes the device according to embodiment A3 or A4, wherein the right ventricular electrode is implantable at the base of the patient's heart proximate to the right bundle branch and the ventricular electrode is implantable at the base of the patient's heart proximate to the left bundle branch.

In embodiment A6, a device includes the device according to any one of embodiments A1-A3, further including a tissue-penetrating electrode assembly coupled to the intracardiac housing and including the ventricular electrode, wherein the tissue-penetrating electrode assembly does not deliver the ventricular electrode into the blood volume of the left ventricle.

In embodiment A7, a device includes the device according to any one of embodiments A1-A3, further including a tissue-penetrating electrode assembly having a helix electrode assembly including the ventricular electrode.

In embodiment A8, a device includes the device according to any one of embodiments A1-A3, further including a tissue-penetrating electrode assembly having a dart electrode assembly including the ventricular electrode.

In embodiment A9, a device includes the device according to any preceding A embodiment, wherein the right atrial electrode is implantable in the endocardium of the right atrium of the patient's heart.

In embodiment A10, a device includes the device according to any preceding A embodiment, wherein the ventricular electrode is implantable in the endocardium of the left ventricle of the patient's heart.

In embodiment A11, a device includes the device according to any preceding A embodiment, wherein the ventricular electrode is implantable through the ventricular septal wall in the right ventricle into the endocardium of the left ventricle.

In embodiment A12, a device includes the device according to any preceding A embodiment, wherein the ventricular electrode is implantable in the ventricular septal wall proximate to the apex of the patient's heart, proximate to the mid-septal portion of the patient's heart, or proximate to the base of the patient's heart.

In embodiment A13, a device includes the device according to any preceding A embodiment, further including a fixation assembly operably coupled to the intracardiac housing couplable to the endocardium of the right ventricle.

In embodiment A14, a device includes the device according to any preceding A embodiment, wherein the controller further includes a wireless communication interface operably couplable to an extravascular implantable medical device, wherein the controller is further configured to monitor electrical activity using the extravascular implantable medical device.

In embodiment A15, a device includes the device according to any preceding A embodiment, wherein to deliver cardiac therapy, the controller is further configured to deliver three-chamber synchronous pacing for the left ventricle, the right ventricle, and the right atrium using the plurality of electrodes.

In embodiment B1, an implantable medical system includes:
an intracardiac housing implantable in a right ventricle of a patient's heart;
an implantable medical lead implantable into the right atrium of a patient's heart;
a plurality of electrodes including:
a ventricular electrode coupled to the intracardiac housing and implantable in the ventricular septal wall of the patient's heart to deliver cardiac therapy to or sense electrical activity of the left ventricle of the patient's heart; and
a right atrial electrode coupled to the lead and implantable to deliver cardiac therapy to or sense electrical activity of the right atrium of the patient's heart;
a first controller contained in the intracardiac housing and including processing circuitry operably coupled to the ventricular electrode; and
a second controller coupled to the implantable medical lead and including processing circuitry operably coupled to the right atrial electrode;
wherein the first controller is configured to wirelessly communicate with the second controller to:
monitor electrical activity using one or both of the right atrial electrode and the ventricular electrode; and
deliver cardiac therapy based on the monitored electrical activity.

In embodiment B2, a system includes the system according to embodiment B1, further including a plurality of external electrodes to provide electrical heterogeneity information.

In embodiment B3, a system includes the system according to embodiment B1 or B2, wherein delivering cardiac therapy includes delivering cardiac resynchronization therapy.

In embodiment B4, a system includes the system according to any preceding B embodiment, further including a right ventricular electrode coupled to the intracardiac housing and implantable to deliver cardiac therapy to or sense electrical activity of the right ventricle of the patient's heart.

In embodiment B5, the system includes the system according to embodiment B4, further including a tissue-penetrating electrode assembly comprising the right ventricular electrode and the ventricular electrode distal to the right ventricular electrode.

In embodiment B6, a system includes the system according to embodiment B4 or B5, wherein the right ventricular electrode is implantable at the base of the patient's heart proximate to the right bundle branch and the ventricular electrode is implantable at the base of the patient's heart proximate to the left bundle branch.

In embodiment B7, a system includes the system according to any one of embodiments B1-B4, further including a tissue-penetrating electrode assembly coupled to the intracardiac housing and including the ventricular electrode, wherein the tissue-penetrating electrode assembly does not deliver the ventricular electrode into the blood volume of the left ventricle.

In embodiment B8, a system includes the system according to any one of embodiments B1-B4, further including a tissue-penetrating electrode assembly having a helix electrode assembly including the ventricular electrode.

In embodiment B9, a system includes the system according to any one of embodiments B1-B4, further including a tissue-penetrating electrode assembly having a dart electrode assembly including the ventricular electrode.

In embodiment B10, a system includes the system according to any preceding B embodiment, wherein the right atrial electrode is implantable in the endocardium of the right atrium of the patient's heart.

In embodiment B11, a system includes the system according to any preceding B embodiment, wherein the ventricular electrode is implantable in the endocardium of the left ventricle of the patient's heart.

In embodiment B12, a system includes the system according to any preceding B embodiment, wherein the ventricular electrode is implantable through the ventricular septal wall in the right ventricle into the endocardium of the left ventricle.

In embodiment B13, a system includes the system according to any preceding B embodiment, wherein the ventricular electrode is implantable in the ventricular septal wall proximate to the apex of the patient's heart, proximate to the mid-septal portion of the patient's heart, or proximate to the base of the patient's heart.

In embodiment B14, a system includes the system according to any preceding B embodiment, further including a fixation assembly operably coupled to the intracardiac housing couplable to the endocardium of the right ventricle.

In embodiment B15, a system includes the system according to any preceding B embodiment, wherein to deliver cardiac therapy, the first controller is further configured to wirelessly communicate with the second controller to deliver three-chamber synchronous pacing for the left ventricle, the right ventricle, and the right atrium using the plurality of electrodes.

In embodiment C1, an implantable medical device includes:
an implantable medical housing for a patient's heart;
a first medical lead coupled to the implantable medical housing and implantable in the ventricular septal wall through the right ventricle of the patient's heart;
a second medical lead coupled to the implantable medical housing and implantable in the right atrium of the patient's heart;
a plurality of electrodes including:
a left ventricular electrode coupled to the first medical lead and implantable in the ventricular septal wall of the patient's heart to deliver cardiac therapy to or sense electrical activity of the left ventricle of the patient's heart;
a right ventricular electrode coupled to the first medical lead and implantable in the ventricular septal wall of the patient's heart to deliver cardiac therapy to or sense electrical activity of the right ventricle of the patient's heart; and
a right atrial electrode coupled to the second medical lead and implantable to deliver cardiac therapy to or sense electrical activity of the right atrium of the patient's heart; and
a controller including processing circuitry operably coupled to the ventricular electrode and to the right atrial electrode, the controller configured to:
monitor electrical activity using one or more of the left ventricular electrode, the right ventricular electrode, and the right atrial electrode; and
deliver cardiac therapy based on the monitored electrical activity.

In embodiment C2, a device includes the device according to embodiment C1, wherein to deliver cardiac therapy, the controller is further configured to deliver three-chamber synchronous pacing for the left ventricle, the right ventricle, and the right atrium using the first medical lead and the second medical lead.

In embodiment C3, a device includes the device according to embodiment C1 or C2, wherein delivering cardiac therapy includes delivering cardiac resynchronization therapy.

In embodiment C4, a device includes the device according to any preceding C embodiment, further including a tissue-penetrating electrode assembly including the right ventricular electrode and the left ventricular electrode distal to the right ventricular electrode.

In embodiment C5, a device includes the device according to any preceding C embodiment, wherein the right ventricular electrode is implantable at the base of the patient's heart proximate to the right bundle branch and the left ventricular electrode is implantable at the base of the patient's heart proximate to the left bundle branch.

In embodiment C6, a device includes the device according to any one of embodiments C1-C3, further including a tissue-penetrating electrode assembly coupled to the first medical lead including the left ventricular electrode, wherein the tissue-penetrating electrode assembly does not deliver the left ventricular electrode into the blood volume of the left ventricle.

In embodiment C7, a device includes the device according to any one of embodiments C1-C3, further including a tissue-penetrating electrode assembly having a helix electrode assembly including the left ventricular electrode.

In embodiment C8, a device includes the device according to any one of embodiments C1-C3, further comprising a tissue-penetrating electrode assembly having a dart electrode assembly including the left ventricular electrode.

In embodiment C9, a device includes the device according to any preceding C embodiment, wherein the right atrial electrode is implantable in the endocardium of the right atrium of the patient's heart.

In embodiment C10, a device includes the device according to any preceding C embodiment, wherein the left ventricular electrode is implantable in the endocardium of the left ventricle of the patient's heart.

In embodiment C11, a device includes the device according to any preceding C embodiment, wherein the left ventricular electrode is implantable through the ventricular septal wall in the right ventricle into the endocardium of the left ventricle.

In embodiment C12, a device includes the device according to any preceding C embodiment, wherein the left ventricular electrode is implantable in the ventricular septal wall proximate to the apex of the patient's heart, proximate to the mid-septal portion of the patient's heart, or proximate to the base of the patient's heart.

In embodiment C13, a device includes the device according to any preceding C embodiment, further including a fixation assembly operably coupled to the first medical lead couplable to the endocardium of the right ventricle.

In embodiment C14, a device includes the device according to any preceding C embodiment, wherein the controller further includes a wireless communication interface operably couplable to an extravascular implantable medical device, wherein the controller is further configured to monitor electrical activity using the extravascular implantable medical device.

In embodiment D1, a method includes:
implanting a ventricular electrode coupled to an intracardiac housing or a first medical lead to the ventricular septal wall of a patient's heart to deliver cardiac therapy to or sense electrical activity of the ventricle of the patient's heart;
implanting a right atrial electrode coupled to a leadlet or a second medical lead in the right atrium of the patient's heart to deliver cardiac therapy to or sense electrical activity of the right atrium of the patient's heart;
monitoring electrical activity using the ventricular electrode, the right atrial electrode, or both; and
delivering cardiac therapy based on the monitored electrical activities using at least one of the ventricular electrode or the right atrial electrode.

In embodiment D2, a method includes the method according to embodiment D1, further including:
testing a pacing parameter or location of the ventricular electrode at a potential implant location using electrical activity monitored by a plurality of external electrodes; and
updating the pacing parameter or location of the ventricular electrode based on the testing.

In embodiment D3, a method includes the method according to embodiment D2, further including introducing a testing catheter along a retrograde path through the aorta of the patient to the left ventricle, wherein testing the pacing parameter or location of the ventricular electrode includes evaluating different locations of the testing catheter along the ventricular septal wall.

In embodiment D4, a method includes the method according to any preceding D embodiment, further including implanting a right ventricular electrode coupled to the intracardiac housing or the first medical lead to the ventricular septal wall of a patient's heart to deliver cardiac therapy to or sense electrical activity of the ventricle of the patient's heart.

In embodiment D5, a method includes the method according to any preceding D embodiment, further including delivering one or more of the electrodes along a path through the superior vena cava of the patient.

Thus, IMPLANTABLE MEDICAL SYSTEMS AND METHODS FOR AV SYNCHRONOUS SEPTAL PACING are disclosed. Although reference is made herein to the accompanying set of drawings that form part of this disclosure, one of at least ordinary skill in the art will appreciate that various adaptations and modifications are within, or do not depart from, the scope of this disclosure. For example, parts of the systems, apparatus, devices, methods, and the like described herein may be combined in a variety of ways with each other. Therefore, it is to be understood that, within the scope of the appended claims, the claimed invention may be practiced other than as explicitly described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

The described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

Terms related to orientation, such as "proximal" or "distal," are used to describe relative positions of components and are not meant to limit the orientation of the components described.

As used herein, the term "configured to" may be used interchangeably with the terms "adapted to" or "structured to" unless the content of this disclosure clearly dictates otherwise.

Th singular forms "a," "an," and "the" encompass singular and plural referents unless its context clearly dictates otherwise.

The phrases "at least one of," "comprises at least one of," and "one or more of" followed by a list refers to any one of the items in the list and any combination of two or more items in the list.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

What is claimed is:

1. An implantable medical device comprising:
    an implantable medical housing;
    a first medical lead coupled to the implantable medical housing and implantable in the right ventricle of a patient's heart, wherein the first medical lead comprises a fixation assembly, wherein the fixation assembly comprises:
        a tissue-penetrating electrode assembly comprising a right ventricular electrode and a left ventricular electrode distal to the right ventricular electrode, wherein the left ventricular electrode is implantable in the ventricular septal wall of the patient's heart to deliver cardiac therapy to or sense electrical activity of the left ventricle of the patient's heart; and
        wherein the right ventricular electrode is implantable in the ventricular septal wall of the patient's heart to deliver cardiac therapy to or sense electrical activity of the right ventricle of the patient's heart;

a second medical lead coupled to the implantable medical housing and implantable in the right atrium of the patient's heart, wherein the second medical lead comprises a right atrial electrode implantable to deliver cardiac therapy to or sense electrical activity of the right atrium of the patient's heart; and a controller comprising processing circuitry operably coupled to the left ventricular electrode, the right ventricular electrode, and the right atrial electrode, the controller configured to:

monitor electrical activity using one or more of the left ventricular electrode, the right ventricular electrode, and the right atrial electrode; and deliver cardiac therapy based on the monitored electrical activity.

2. The device according to claim 1, wherein to deliver cardiac therapy, the controller is further configured to deliver three-chamber synchronous pacing for the left ventricle, the right ventricle, and the right atrium using the first medical lead and the second medical lead.

3. The device according to claim 1, wherein delivering cardiac therapy comprises delivering cardiac resynchronization therapy.

4. The device according to claim 1, wherein the tissue-penetrating electrode assembly does not deliver the left ventricular electrode into the blood volume of the left ventricle.

5. The device according to claim 1, wherein the right ventricular electrode is implantable at the base of the patient's heart proximate to the right bundle branch and the left ventricular electrode is implantable at the base of the patient's heart proximate to the left bundle branch.

6. The device according to claim 1, wherein the first medical lead comprises a helix comprising at least the left ventricular electrode.

7. The device according to claim 1, further comprising a dart electrode assembly coupled to the first medical lead including the left ventricular electrode.

8. The device according to claim 1, wherein the right atrial electrode is implantable in the endocardium of the right atrium of the patient's heart.

9. The device according to claim 1, wherein the left ventricular electrode is implantable in the endocardium of the left ventricle of the patient's heart.

10. The device according to claim 1, wherein the left ventricular electrode is implantable through the ventricular septal wall in the right ventricle into the endocardium of the left ventricle.

11. The device according to claim 1, wherein the left ventricular electrode is implantable in the ventricular septal wall proximate to the apex of the patient's heart, proximate to the mid-septal portion of the patient's heart, or proximate to the base of the patient's heart.

12. The device according to claim 1, wherein the controller further comprises a wireless communication interface operably couplable to an extravascular implantable medical device, wherein the controller is further configured to monitor electrical activity using the extravascular implantable medical device.

13. A method comprising:

implanting a ventricular electrode coupled to an intracardiac housing or a first medical lead to the ventricular septal wall of a patient's heart to deliver cardiac therapy to or sense electrical activity of a ventricle of the patient's heart;

implanting a right atrial electrode coupled to a leadlet or a second medical lead in the right atrium of the patient's heart to deliver cardiac therapy to or sense electrical activity of the right atrium of the patient's heart;

monitoring electrical activity using the ventricular electrode, the right atrial electrode, or both;

testing a pacing parameter or location of the ventricular electrode at a potential implant location using electrical heterogeneity information monitored by a plurality of external electrodes;

updating the pacing parameter or location of the ventricular electrode based on the testing; and delivering cardiac therapy based on the monitored electrical activities using at least one of the ventricular electrode or the right atrial electrode.

14. The method according to claim 13, further comprising introducing a testing catheter along a retrograde path through the aorta of the patient to the left ventricle, wherein testing the pacing parameter or location of the ventricular electrode comprises evaluating different locations of the testing catheter along the ventricular septal wall.

15. The method according to claim 13, further comprising implanting a right ventricular electrode coupled to the intracardiac housing or the first medical lead to the ventricular septal wall of a patient's heart to deliver cardiac therapy to or sense electrical activity of the ventricle of the patient's heart.

16. The method according to claim 13, further comprising delivering one or more of the electrodes along a path through the superior vena cava of the patient.

* * * * *